United States Patent
Ohashi et al.

(10) Patent No.: US 9,848,840 B2
(45) Date of Patent: Dec. 26, 2017

(54) X-RAY DIAGNOSTIC APPARATUS COMPRISING AN X-RAY FILTER MOVABLE ALONG AN IMAGING AXIS OF X-RAYS

(71) Applicant: TOSHIBA MEDICAL SYSTEMS CORPORATION, Otawara-shi (JP)

(72) Inventors: Shumpei Ohashi, Otawara (JP); Yoshimasa Kobayashi, Nasushiobara (JP); Koichiro Watanabe, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 48 days.

(21) Appl. No.: 14/480,794

(22) Filed: Sep. 9, 2014

(65) Prior Publication Data
US 2015/0078516 A1 Mar. 19, 2015

(30) Foreign Application Priority Data
Sep. 19, 2013 (JP) .................... 2013-194644

(51) Int. Cl.
- A61B 6/00 (2006.01)
- A61B 6/03 (2006.01)
- G21K 3/00 (2006.01)
- A61B 6/06 (2006.01)

(52) U.S. Cl.
CPC ............ *A61B 6/4035* (2013.01); *A61B 6/032* (2013.01); *A61B 6/06* (2013.01); *A61B 6/40* (2013.01); *A61B 6/4042* (2013.01); *A61B 6/486* (2013.01); *A61B 6/487* (2013.01); *A61B 6/542* (2013.01); *A61B 6/4441* (2013.01)

(58) Field of Classification Search
CPC .. A61B 6/032; A61B 6/06; A61B 6/40; A61B 6/4035; A61B 6/4042; A61B 6/4441; A61B 6/486; A61B 6/487; A61B 6/542
USPC .................... 378/16, 42, 156–159
See application file for complete search history.

(56) References Cited

U.S. PATENT DOCUMENTS

| 4,277,685 A | * | 7/1981 | Covic | G03B 42/02 378/150 |
| 4,399,550 A | * | 8/1983 | Hauck | A61B 6/06 378/157 |

(Continued)

FOREIGN PATENT DOCUMENTS

| JP | 3-193042 A | 8/1991 |
| JP | 2006-288554 A | 10/2006 |
| JP | 2011-19712 A | 2/2011 |

OTHER PUBLICATIONS

Office Action dated May 16, 2017 in Japanese Patent Application No. 2013-194644.

*Primary Examiner* — Allen C. Ho
(74) *Attorney, Agent, or Firm* — Oblon, McClelland, Maier & Neustadt, L.L.P.

(57) ABSTRACT

According to one embodiment, an X-ray diagnostic apparatus includes an X-ray tube, an X-ray detection unit, an X-ray filter, an input unit, and an X-ray filter support unit. The X-ray tube generates X-rays. The X-ray detection unit detects the X-rays transmitted through a subject. The X-ray filter is arranged between the X-ray tube and the object and has an opening. The X-ray filter support unit supports the X-ray filter so as to make the X-ray filter movable in an imaging axis direction of the X-rays.

17 Claims, 18 Drawing Sheets

(56) References Cited

U.S. PATENT DOCUMENTS

| | | | | |
|---|---|---|---|---|
| 5,107,529 A * | 4/1992 | Boone | A61B 6/4035 | 359/890 |
| 6,036,362 A * | 3/2000 | Schmitt | A61B 6/08 | 378/150 |
| 6,094,474 A * | 7/2000 | Vezina | G21K 1/10 | 378/156 |
| 6,226,352 B1 * | 5/2001 | Salb | A61B 6/4035 | 378/143 |
| 6,280,084 B1 * | 8/2001 | Toth | A61B 6/032 | 378/158 |
| 6,307,918 B1 * | 10/2001 | Toth | A61B 6/032 | 378/156 |
| 6,501,828 B1 * | 12/2002 | Popescu | A61B 6/06 | 378/145 |
| 6,597,758 B1 * | 7/2003 | Rosner | G01N 23/04 | 378/156 |
| 6,614,878 B2 * | 9/2003 | Bogatu | A61B 6/4042 | 378/156 |
| 6,633,627 B2 * | 10/2003 | Horiuchi | A61B 6/032 | 378/156 |
| 6,650,730 B2 * | 11/2003 | Bogatu | A61B 6/4042 | 378/156 |
| 6,836,535 B2 * | 12/2004 | Toth | A61B 6/032 | 378/156 |
| 6,851,854 B2 * | 2/2005 | Schmitt | A61B 6/06 | 250/252.1 |
| 6,862,340 B2 * | 3/2005 | Wurzer | G21K 1/10 | 250/505.1 |
| 6,898,271 B2 * | 5/2005 | Akutsu | A61B 6/06 | 378/157 |
| 6,950,492 B2 * | 9/2005 | Besson | A61B 6/508 | 378/16 |
| 6,968,030 B2 * | 11/2005 | Hoffman | A61B 6/032 | 378/158 |
| 6,990,171 B2 * | 1/2006 | Toth | A61B 6/032 | 378/158 |
| 7,046,756 B2 * | 5/2006 | Hoffman | A61B 6/032 | 378/158 |
| 7,050,544 B2 * | 5/2006 | Karlsson | A61B 6/502 | 378/148 |
| 7,068,750 B2 * | 6/2006 | Toth | A61B 6/032 | 378/156 |
| 7,068,751 B2 * | 6/2006 | Toth | A61B 6/032 | 378/20 |
| 7,072,447 B2 * | 7/2006 | Graf | G21K 1/10 | 378/156 |
| 7,076,029 B2 * | 7/2006 | Toth | A61B 6/032 | 378/158 |
| 7,082,189 B2 * | 7/2006 | Yahata | A61B 6/06 | 378/156 |
| 7,092,490 B2 * | 8/2006 | Saladin | A61B 6/4035 | 356/418 |
| 7,120,222 B2 * | 10/2006 | Hoffman | A61B 6/032 | 378/124 |
| 7,170,975 B2 * | 1/2007 | Distler | A61B 6/032 | 378/147 |
| 7,187,756 B2 * | 3/2007 | Gohno | G01N 23/046 | 378/124 |
| 7,254,216 B2 * | 8/2007 | Thandiackal | A61B 6/032 | 378/157 |
| 7,308,073 B2 * | 12/2007 | Tkaczyk | G21K 1/10 | 378/156 |
| 7,313,217 B2 * | 12/2007 | Toth | A61B 6/032 | 378/20 |
| 7,330,535 B2 * | 2/2008 | Arenson | G21K 1/04 | 378/156 |
| 7,430,282 B2 * | 9/2008 | Mori | A61B 6/032 | 378/145 |
| 7,463,715 B2 * | 12/2008 | Spahn | A61B 6/4035 | 378/114 |
| 7,636,413 B2 * | 12/2009 | Toth | A61B 6/032 | 378/157 |
| 7,649,981 B2 * | 1/2010 | Seppi | A61B 6/032 | 378/124 |
| 7,653,179 B2 * | 1/2010 | Ramsauer | A61B 6/06 | 378/157 |
| 7,680,249 B2 * | 3/2010 | Yuan | A61B 6/00 | 378/156 |
| 7,869,862 B2 * | 1/2011 | Seppi | A61B 6/032 | 600/420 |
| 8,077,830 B2 * | 12/2011 | Brown | A61N 5/1048 | 378/156 |
| 8,218,721 B2 * | 7/2012 | Raupach | A61B 6/032 | 378/150 |
| 8,218,728 B2 * | 7/2012 | Karch | A61B 6/032 | 378/156 |
| 8,284,903 B2 * | 10/2012 | Yuan | A61B 6/06 | 378/156 |
| 8,553,835 B2 * | 10/2013 | Hangartner | A61B 6/032 | 378/157 |
| 8,571,178 B2 * | 10/2013 | Sendai | A61B 6/4042 | 378/157 |
| 8,798,230 B2 * | 8/2014 | Cho | A61B 6/405 | 378/15 |
| 8,929,678 B2 * | 1/2015 | jvari | | 378/51 |
| 8,942,341 B2 * | 1/2015 | Hsieh | A61B 6/032 | 378/158 |
| 9,008,264 B2 * | 4/2015 | Boone | A61B 6/583 | 378/207 |
| 9,254,109 B2 * | 2/2016 | Becker | A61B 6/032 | |
| 9,480,443 B2 * | 11/2016 | Feuerlein | A61B 6/032 | |
| 9,504,439 B2 * | 11/2016 | Yi | A61B 6/5205 | |

* cited by examiner

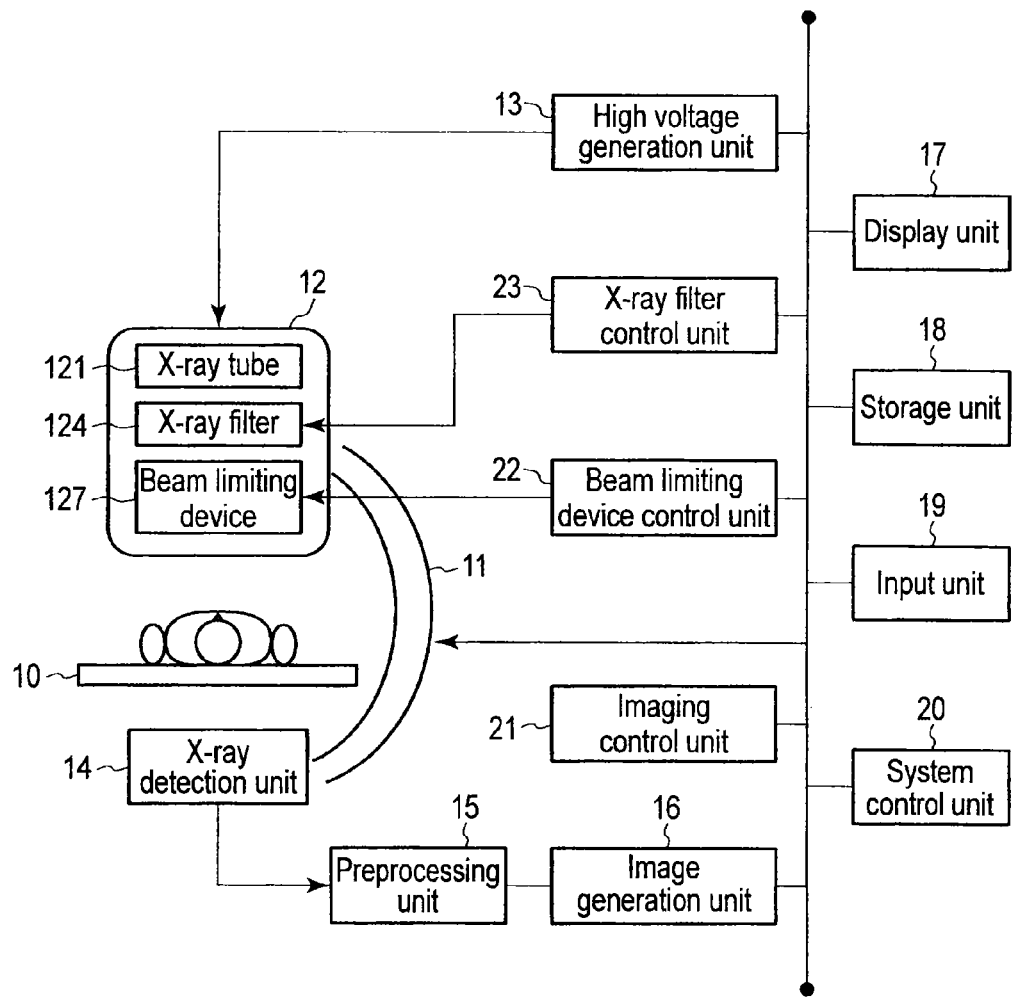
F I G. 1

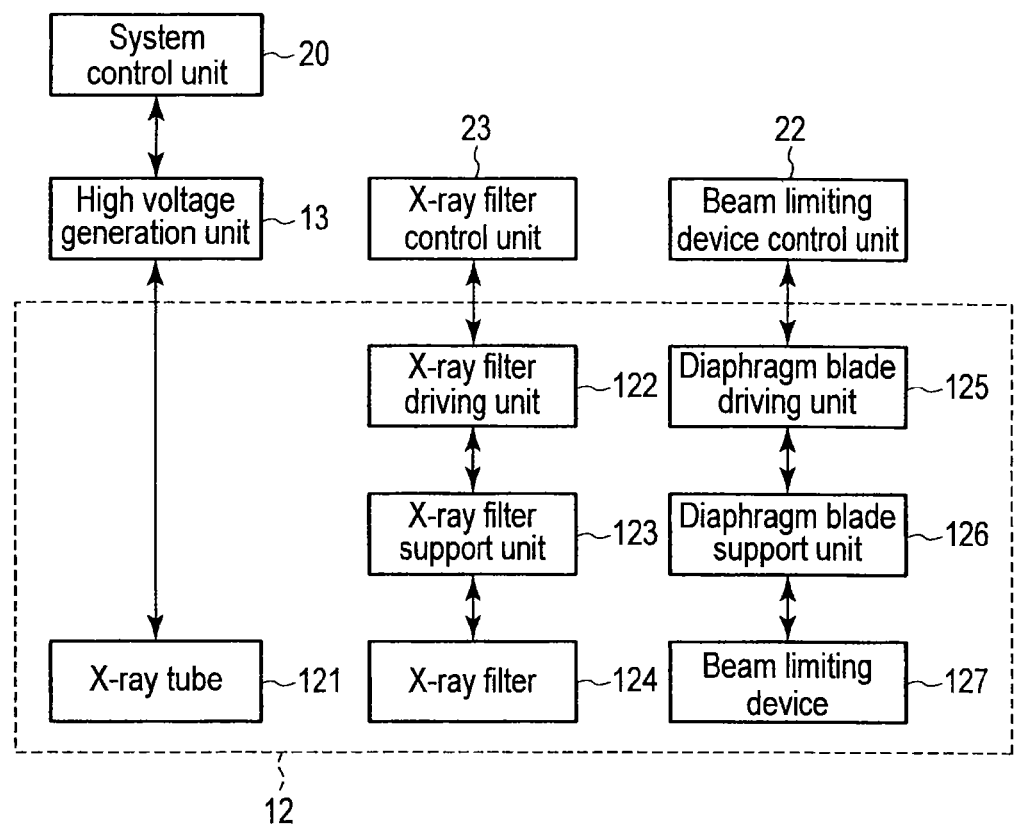
F I G. 2

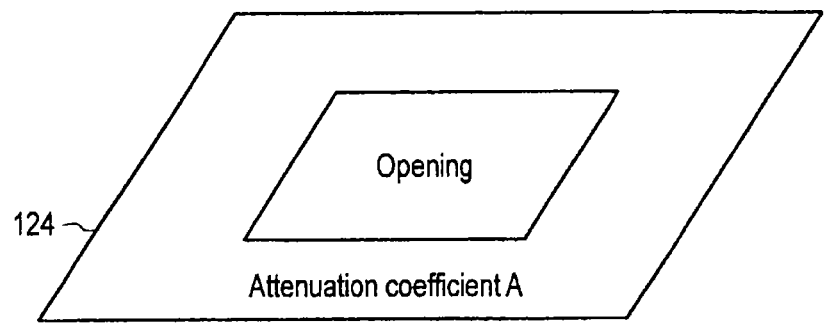
F I G. 3A
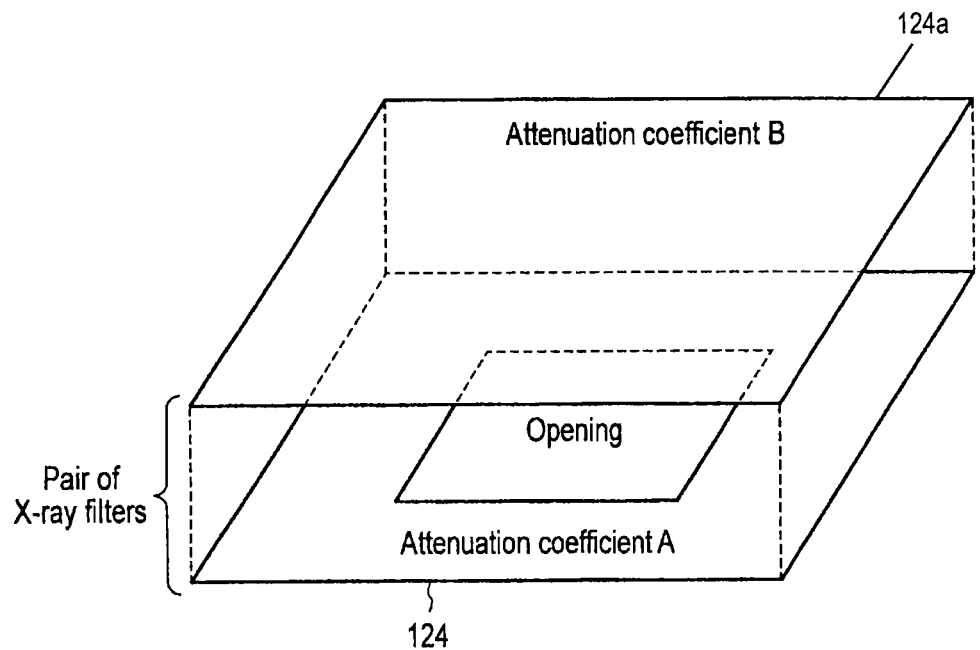
F I G. 3B

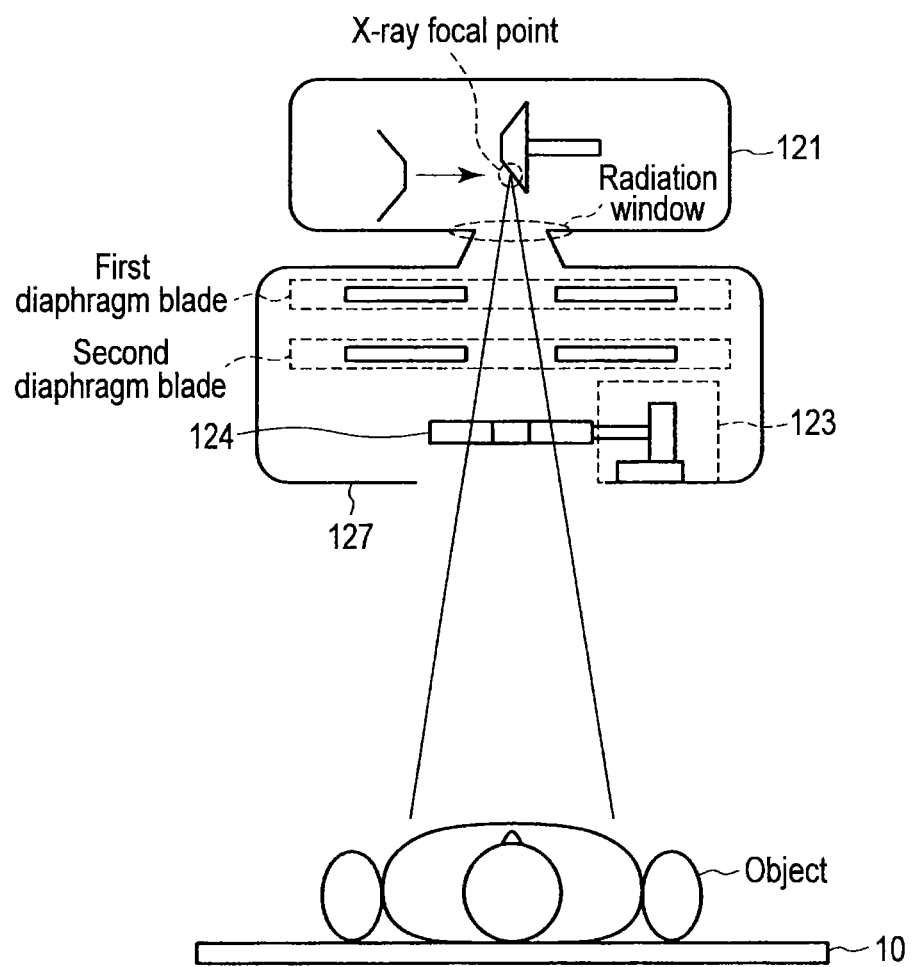
F I G. 6

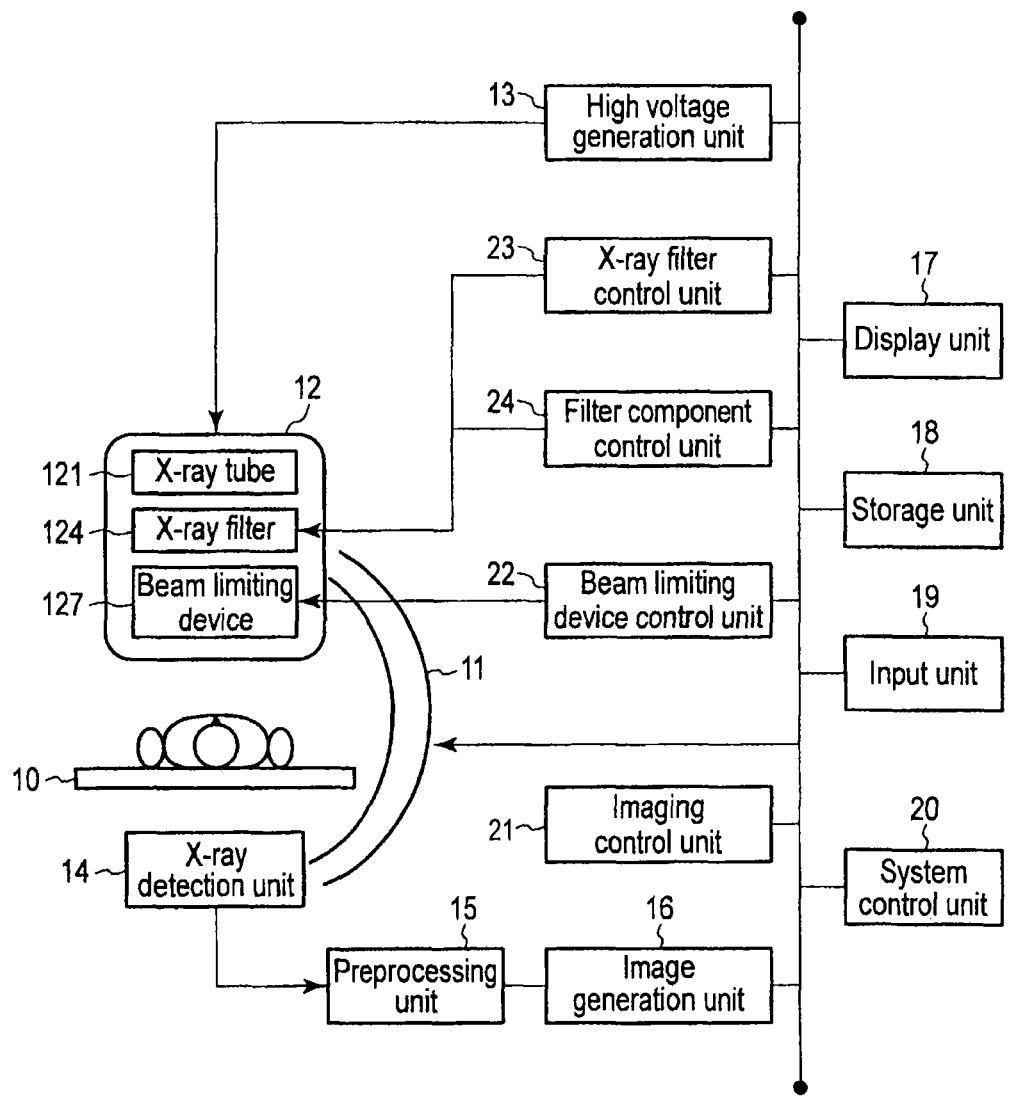
F I G. 11

F I G. 14A
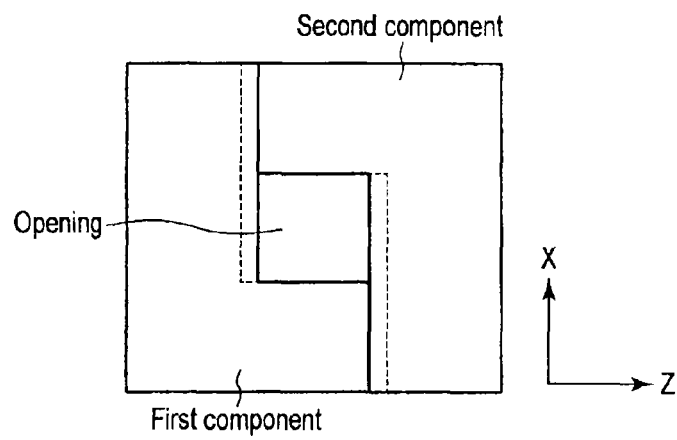
F I G. 14B
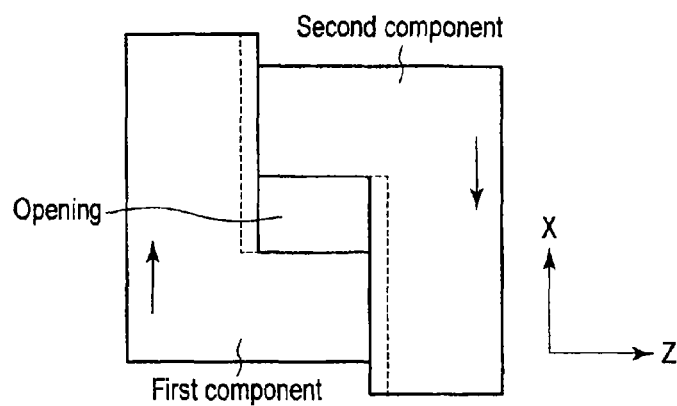
F I G. 14C
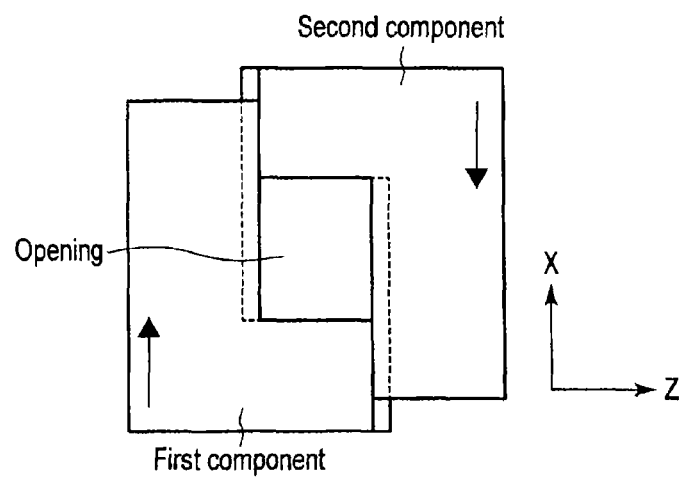

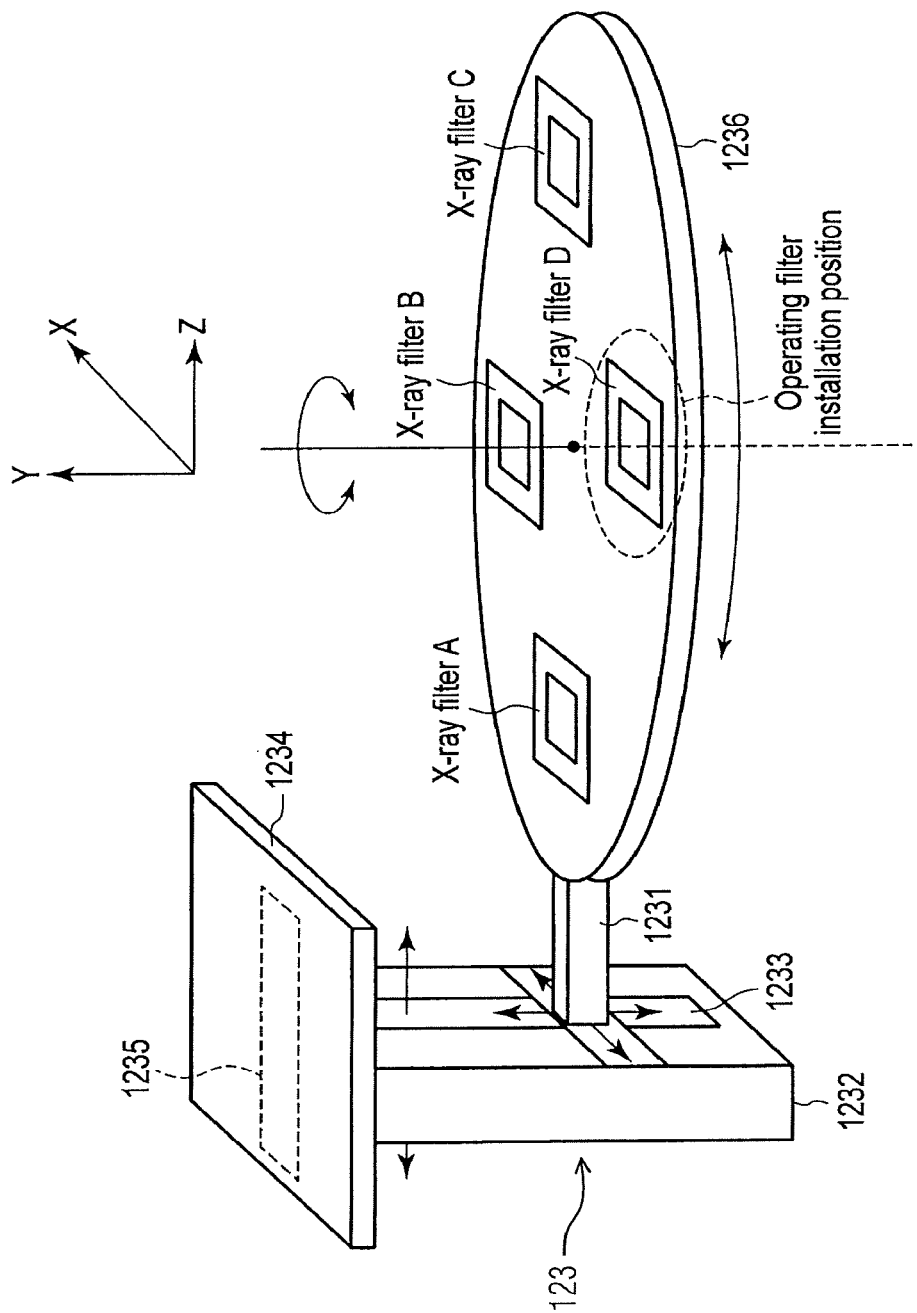
F I G. 17

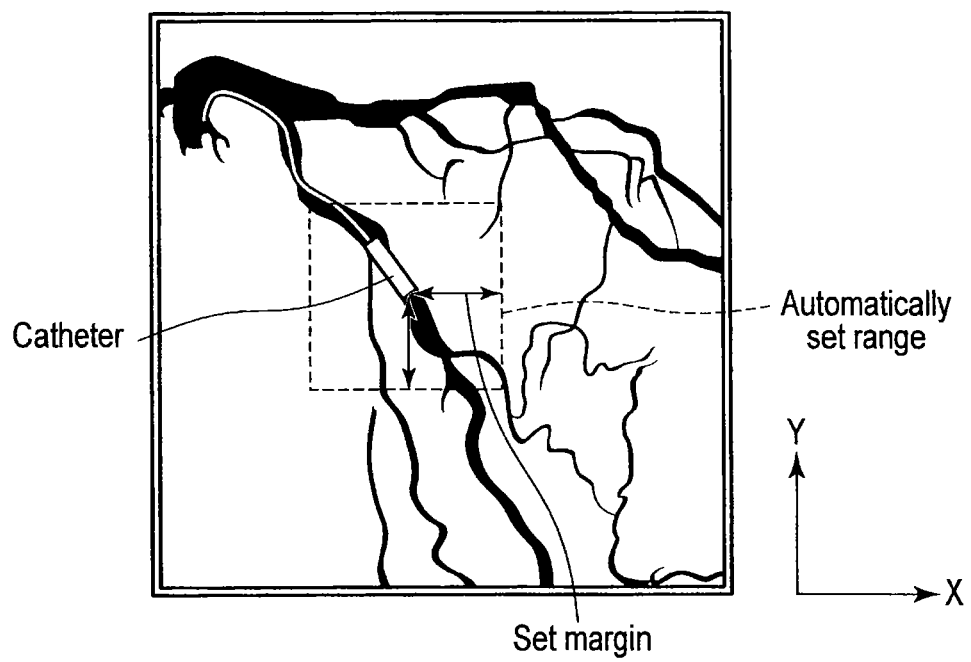
F I G. 20

X-RAY DIAGNOSTIC APPARATUS COMPRISING AN X-RAY FILTER MOVABLE ALONG AN IMAGING AXIS OF X-RAYS

CROSS-REFERENCE TO RELATED APPLICATIONS

This application is based upon and claims the benefit of priority from the prior Japanese Patent Application No. 2013-194644, filed Sep. 19, 2013 the entire contents of which are incorporated herein by reference.

FIELD

Embodiments described herein relate generally to an X-ray diagnostic apparatus.

BACKGROUND

X-ray fluoroscopy using an X-ray diagnostic apparatus is a technique of providing a user with a fluoroscopic image concerning an object, which is updated in real time. The user can observe the state of a moving organ, the manner of the flow of a contrast medium, and the like by visually recognizing the fluoroscopic image. In X-ray fluoroscopy, however, a portion around a region of interest of the object is irradiated with the same dose of X-rays as that for the region of interest, unnecessary exposure of the object to X-rays poses a problem. There is available spot fluoroscopy as a technique of suppressing such unnecessary exposure. Spot fluoroscopy is a technique of providing the user with the superimposed image obtained by superimposing a fluoroscopic image corresponding to a region of interest of an object, which is updated in real time, on a still image corresponding to a specific region of the object which is acquired by conventional X-ray fluoroscopy immediately before spot fluoroscopy. The user can observe the region of interest in real time while checking the position and the like of the region of interest in the specific region by visually recognizing the superimposed image. The irradiation range of X-rays under spot fluoroscopy is only a region of interest. It is therefore possible to suppress unnecessary exposure of an object as compared with conventional X-ray fluoroscopy. However, spot fluoroscopy does not allow real-time observation of a portion around a region of interest.

For this reason, there is a demand for real-time observation of also a portion around a region of interest while reducing the exposure dose of an object more than the related art. In order to meet this demand, it is a challenge to develop a technique of reducing the dose of X-rays on a portion around a region of interest relative to the dose of X-rays on the region of interest.

BRIEF DESCRIPTION OF THE DRAWINGS

FIG. 1 is a block diagram showing the arrangement of an X-ray diagnostic apparatus according to the first embodiment;

FIG. 2 is a block diagram showing the arrangement of the X-ray irradiation system of the X-ray diagnostic apparatus according to the first embodiment;

FIG. 3A is a view showing the first example of the X-ray filter of the X-ray diagnostic apparatus according to the first embodiment;

FIG. 3B is a view showing a pair of X-ray filters incorporating the X-ray filter 124 according to the first example shown in FIG. 3A;

FIG. 6 is a view showing the second arrangement example of the X-ray filter of the X-ray diagnostic apparatus according to the first embodiment;

FIG. 11 is a block diagram showing the arrangement of an X-ray diagnostic apparatus according to the second embodiment;

FIG. 14A is a view showing the first example of the X-ray filter before the opening is changed;

FIG. 14B is a view showing the first example in which the opening of the X-ray filter shown in FIG. 14A is changed;

FIG. 14C is a view showing the second example in which the opening of the X-ray filter shown in FIG. 14A is changed;

FIG. 17 is a perspective view showing an example of the structure of the X-ray filter support unit of the X-ray diagnostic apparatus according to the third embodiment;

FIG. 20 is a view for explaining the automatically set range set by the X-ray filter control unit of the X-ray diagnostic apparatus according to the fourth embodiment.

DETAILED DESCRIPTION

Figure 4:
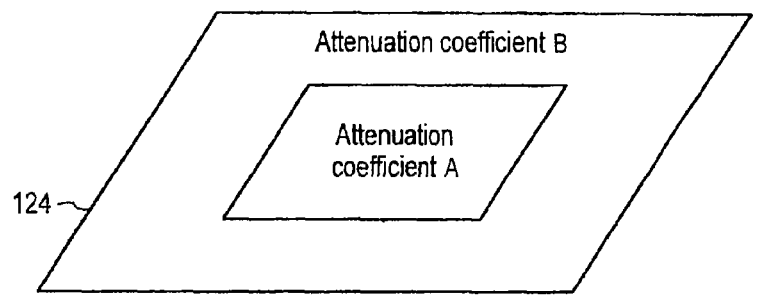
FIG. 4 is a view showing the second example of the X-ray filter of the X-ray diagnostic apparatus according to the first embodiment.

An X-ray diagnostic apparatus according to an embodiment includes an X-ray tube, an X-ray detection unit, an X-ray filter, and an X-ray filter support unit. The X-ray tube generates X-rays. The X-ray detection unit detects the X-rays generated from the X-ray tube and transmitted through an object. The X-ray filter has an opening and is arranged between the X-ray tube and the object. The X-ray filter support unit supports the X-ray filter so as to make it movable in the imaging axis direction of the X-rays.

X-ray diagnostic apparatuses according the first to fourth embodiments will be described below with reference to the accompanying drawings. Note that in the following description, the same reference numerals denote constituent elements having almost the same functions and arrangements, and a repetitive description will be made only when required.

First Embodiment

FIG. 1 is a block diagram showing the arrangement of the X-ray diagnostic apparatus according to the first embodiment. The X-ray diagnostic apparatus according to the first embodiment (to be referred to as the first X-ray diagnostic apparatus hereinafter) includes a bed 10, a C-arm 11, an X-ray irradiation system 12, a high voltage generation unit 13, an X-ray detection unit 14, a preprocessing unit 15, an image generation unit 16, a display unit 17, a storage unit 18, an input unit 19, a system control unit 20, an imaging control unit 21, a beam limiting device control unit 22, and an X-ray filter control unit 23.

The bed 10 movably supports a top (not shown) on which an object is placed. The bed 10 moves the top when a bed driving unit (not shown) is driven under the control of the system control unit 20.

The C-arm 11 is rotatably supported on a C-arm support mechanism (not shown). The C-arm support mechanism has a plurality of rotation axes for rotating the C-arm 11. The C-arm 11 is rotated about the plurality of rotation axes when a C-arm driving unit (not shown) included in the C-arm support mechanism is driven under the control of the system control unit 20. The C-arm 11 holds the X-ray irradiation system 12 at one end.

FIG. 2 is a block diagram showing the arrangement of the X-ray irradiation system 12 of the X-ray diagnostic apparatus according to the first embodiment. As shown in FIG. 2, the X-ray irradiation system 12 includes an X-ray tube 121, an X-ray filter driving unit 122, an X-ray filter support unit 123, an X-ray filter 124, a diaphragm blade driving unit 125, a diaphragm blade support unit 126, and a beam limiting device 127. The X-ray tube 121 is a vacuum tube which generates X-rays.

The X-ray tube 121 generates X-rays from the focal point upon receiving a high voltage (tube voltage) and a tube current from the high voltage generation unit 13. The generated X-rays are radiated from the radiation window of the X-ray tube 121. The X-rays then pass through the X-ray filter 124 and the beam limiting device 127 to irradiate an object.

The X-ray filter 124 changes the radiation quality of X-rays to, for example, reduce the X-ray exposure dose of an object or improve image quality. The X-ray filter 124 removes long-wavelength components unnecessary for diagnosis from the continuous spectrum of X-rays radiated from the radiation window. In addition, the X-ray filter 124 partially reduces the dose of X-rays irradiating the X-ray detection surface of the X-ray detection unit 14 (to be simply referred to as the X-ray detection surface hereinafter) in the irradiation range of X-rays. The X-ray filter 124 includes a moving mechanism. The X-ray filter support unit 123 movably supports the X-ray filter 124. The X-ray filter driving unit 122 drives the moving mechanism of the X-ray filter 124 under the control of the X-ray filter control unit 23. The X-ray filter driving unit 122 is, for example, a driving device such as a motor. The arrangement and movement of the X-ray filter 124 will be described below.

The beam limiting device 127 includes a plurality of diaphragm blades for limiting the X-ray irradiation range on the detection surface of the X-ray detection unit 14 with respect to the X-rays radiated from the radiation window of the X-ray tube 121 and having passed through the X-ray filter 124. The plurality of diaphragm blades respectively have moving mechanisms. The diaphragm blade support unit 126 movably supports the plurality of diaphragm blades. The diaphragm blade driving unit 125 drives the moving mechanism of each diaphragm blade under the control of the beam limiting device control unit 22. The diaphragm blade driving unit 125 is, for example, a driving device such as a motor.

The C-arm 11 holds the X-ray detection unit 14 at the other end to make it face the X-ray irradiation system 12. The X-ray detection unit 14 includes a plurality of X-ray detection elements. The plurality of X-ray detection elements are arrayed two-dimensionally. A detector in the form of a two-dimensional array is called an FPD (Flat Panel Detector). Each X-ray detection element of the FPD detects the X-rays radiated from the X-ray irradiation system 12 and transmitted through an object. Each X-ray detection element of the FPD outputs an electrical signal corresponding to a detected X-ray intensity. Note that an axis connecting the focal point of the X-ray tube 121 and the central position of the X-ray detection surface of the X-ray detection unit 14 is called an imaging axis.

Note that in the first embodiment, the X-ray irradiation system 12 and the X-ray detection unit 14 are held by the C-arm 11, and the C-arm 11 is rotatably supported by the C-arm support mechanism. However, the holding mechanism to be used is not limited to the C-arm 11 as long as the X-ray irradiation system 12 and the X-ray detection unit 14 can be held so as to face each other. For example, the C-arm 11 and the C-arm arm support mechanism may be replaced by a ceiling-mounted Ω arm. Alternatively, the C-arm 11 and the C-arm support mechanism can be replaced by a first holding unit which rotatably holds the X-ray irradiation system 12 and a second holding unit which rotatably holds the X-ray detection unit 14. In this case, for example, the first holding unit is placed on the floor, and the second holding unit is suspended from the ceiling. The first holding unit is held so as to be movable in three axis directions relative to the floor. The second holding unit is held so as to be movable in three axis directions relative to the ceiling. With the above mechanism, it is possible to make the X-ray irradiation system 12 and the X-ray detection unit 14 face each other. It is possible to perform X-ray imaging of an object in all directions by synchronously controlling the rotating operations of the first and second holding units.

The preprocessing unit 15 executes preprocessing for the electrical signal output from the X-ray detection unit 14. The preprocessing includes, for example, various types of correction processing, amplification processing, and A/D conversion processing.

The image generation unit 16 generates X-ray image data based on the electrical signal having undergone the preprocessing. The pixel values assigned to the respective pixels constituting the X-ray image data are, for example, values corresponding to X-ray attenuation coefficients concerning a substance on the transmission path of X-rays.

The display unit 17 displays the X-ray image data generated by the image generation unit 16 on the display screen.

The storage unit 18 is, for example, a semiconductor storage device such as a Flash SSD (Solid State Drive) as a semiconductor storage element or an HDD (Hard Disk Drive). The storage unit 18 stores the X-ray image data generated by the image generation unit 16 and the like.

The input unit 19 functions as an interface with which the user inputs instruction information to the first X-ray diagnostic apparatus. For example, the input unit 19 includes an operation console for moving the C-arm 11 (the X-ray tube 121 and the X-ray detection unit 14) and the top to the imaging position desired by the user. The operation console includes buttons, a handle, and a trackball. The user can move the C-arm 11 to the desired imaging position by operating the operation console so as to independently rotate the C-arm 11 and the C-arm support mechanism about the plurality of rotation axes described above. The input unit 19 includes input devices such as a mouse and a keyboard with which the user sets imaging conditions and a region of interest. Imaging conditions include a tube voltage, tube current, pulse width, pulse rate, imaging count, and imaging range. A region of interest is a partial range of the X-ray image data. The region of interest has higher image quality than another part of the X-ray image data. For example, the region of interest has higher SN-ratio (Signal to Noise ratio) or density resolution than another part of the X-ray image data.

The input unit 19 may have an imaging switch for starting X-ray imaging. The input unit 19 outputs a trigger signal for executing X-ray imaging to the system control unit 20 (to be described later) in response to the operation of the imaging switch by the user.

The system control unit 20 receives the information input from the input unit 19 and temporarily stores the input information in a memory circuit. The system control unit 20 controls each unit of the first X-ray diagnostic apparatus based on this input information. More specifically, the system control unit 20 controls the C-arm driving unit and the bed driving unit based on the imaging conditions set by the user via the input unit 19 and the movement information of the C-arm 11 which is instructed by the user via the operation console.

The imaging control unit 21 controls the high voltage generation unit 13 and the X-ray detection unit 14 based on the data of the imaging conditions set by user instructions via the input unit 19. The high voltage generation unit 13 and the X-ray detection unit 14 operate to execute an imaging operation under the control of the imaging control unit 21.

The beam limiting device control unit 22 controls the diaphragm blade driving unit 125. More specifically, the beam limiting device control unit 22 drives the diaphragm blade driving unit 125 to move each of the plurality of diaphragm blades in order to irradiate the imaging range of the object, which is set by the user via the input unit 19, with X-rays.

The X-ray filter control unit 23 controls the X-ray filter driving unit 122. More specifically, the X-ray filter control unit 23 drives the X-ray filter driving unit 122 to move the X-ray filter 124 in accordance with a user instruction via the input unit 19, an output from the X-ray detection unit 14, and the like.

The X-ray filter 124 of the X-ray diagnostic apparatus according to the first embodiment will be described below with reference to FIGS. 3A, 3B, 4, and 5.

FIG. 3A is a view showing the first example of the X-ray filter 124 of the X-ray diagnostic apparatus according to the first embodiment. The X-ray filter 124 according to the first example shown in FIG. 3A is formed from a metal plate with an attenuation coefficient A and has an opening. For example, the opening is formed such that the central position of the opening overlaps the central position of the overall X-ray filter 124 or its barycentric position. The opening has, for example, a rectangular shape. However, the opening may have a circular shape. The number of openings may be single as shown in FIG. 3A or plural. Note that the X-ray filter 124 according to the first example shown in FIG. 3A may be used in combination with another X-ray filter.

FIG. 3B is a view showing a pair of X-ray filters incorporating the X-ray filter 124 according to the first example shown in FIG. 3A. As shown in FIG. 3B, the X-ray filter 124 is combined with another X-ray filter to form a pair of X-ray filters. The other X-ray filter 124a has an attenuation coefficient B for removing long-wavelength components unnecessary for diagnosis from the continuous spectrum of X-rays radiated from the radiation window. Although FIG. 3B shows an arrangement including one X-ray filter as another X-ray filter, the arrangement may include a plurality of X-ray filters as other X-ray filters. In addition, the X-ray filter 124 according to the first example may be a single component having an opening or may be constituted by a plurality of components. In this case, it is possible to change the size, shape, and the like of the opening by replacing at least one of the plurality of components. In addition, it is possible to make the size of the opening variable by forming the X-ray filter 124 according to the first example using a plurality of components and manually and automatically moving the plurality of components. A structure for automatically making the size of the opening variable and a method of controlling the structure will be described in the second embodiment.

FIG. 4 is a view showing the second example of the X-ray filter 124 of the X-ray diagnostic apparatus according to the first embodiment. The X-ray filter 124 according to the second example shown in FIG. 4 is formed from a metal plate, and has a plurality of portions with different attenuation coefficients. The X-ray filter 124, for example, has a first portion and a second portion contacting the periphery of the first portion in the same plane as shown in FIG. 4. The attenuation coefficient A corresponding to the first portion is smaller than an attenuation coefficient B corresponding to the second portion. Like the X-ray filter 124 according to the first example shown in FIGS. 3A and 3B, the X-ray filter 124 according to the second example shown in FIG. 4 may be combined with another X-ray filter.

The arrangement of the X-ray filter 124 of the X-ray diagnostic apparatus according to the first embodiment will be described next with reference to FIGS. 5 and 6.

Figure 5:
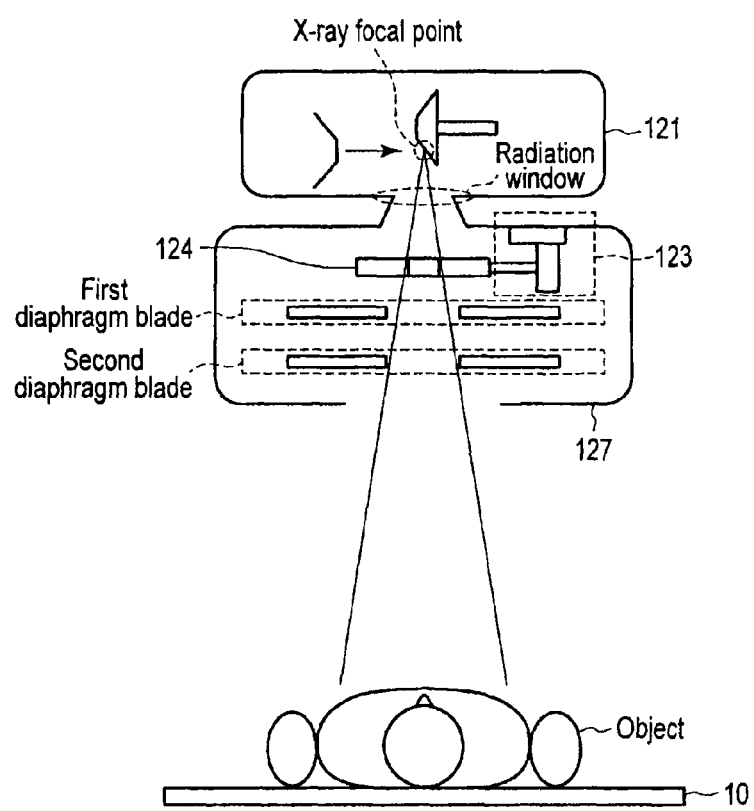
FIG. 5 is a view showing the first arrangement example of the X-ray filter of the X-ray diagnostic apparatus according to the first embodiment.

FIG. 5 is a view showing the first arrangement example of the X-ray filter 124 of the X-ray diagnostic apparatus according to the first embodiment. The X-ray filter 124 is arranged between the X-ray tube 121 and an object. As shown in FIG. 5, the X-ray filter 124 is provided in, for example, the beam limiting device 127 and arranged between the X-ray tube 121 and the first X-ray diaphragm blade and the second X-ray diaphragm blade. According to the above description, the X-ray filter 124 is provided in the beam limiting device 127. However, an X-ray filter 124 may be arranged as a single device between the X-ray tube 121 and the beam limiting device 127. Note that since the X-ray filter 124 is used to, for example, reduce the X-ray exposure dose of an object or improve image quality, the position of the X-ray filter 124 is not limited to that in the example shown in FIG. 5 as long as it is arranged between the object and the X-ray tube 121. For example, the X-ray filter 124 may be arranged outside the beam limiting device 127 or may be arranged between an object and the X-ray diaphragm blades.

FIG. 6 is a view showing the second arrangement example of the X-ray filter 124 of the X-ray diagnostic apparatus according to the first embodiment. As shown in FIG. 6, the X-ray filter 124 is arranged between the X-ray tube 121 and the object as in the first arrangement example shown in FIG. 5. In addition, for example, the X-ray filter 124 is provided in the beam limiting device 127 and arranged between the first X-ray diaphragm blade and the second X-ray diaphragm blade and the object. According to the above description, the X-ray filter 124 is provided in the beam limiting device 127. However, the X-ray filter 124 may be arranged as a single device between the beam limiting device 127 and the object.

As shown in FIG. 5, the size of the X-ray filter 124 can be reduced by arranging it near the X-ray tube 121. In addition, it is possible to reduce the movement amount of the X-ray filter 124 when the user wants to move the X-ray irradiation range corresponding to the opening in the X-ray irradiation range and change the size of the X-ray irradiation range corresponding to the opening. On the other hand, as shown in FIG. 6, since the X-ray filter 124 is arranged between the first X-ray diaphragm blade and the second X-ray diaphragm blade and the object, the movement amount of the X-ray filter 124 in the imaging axis direction is not limited. In addition, it is possible to reduce an error in the position of the X-ray irradiation range corresponding to the opening, which is caused by an error in the arrangement of the X-ray filter 124. That is, since high accuracy is not required concerning the arrangement of the X-ray filter 124, a precision control mechanism is not required. In addition, providing the X-ray filter 124 as a single device will facilitate the mounting of the device.

The movement of the X-ray filter 124 of the X-ray diagnostic apparatus according to the first embodiment will be described next with reference to FIG. 7.

Figure 7:
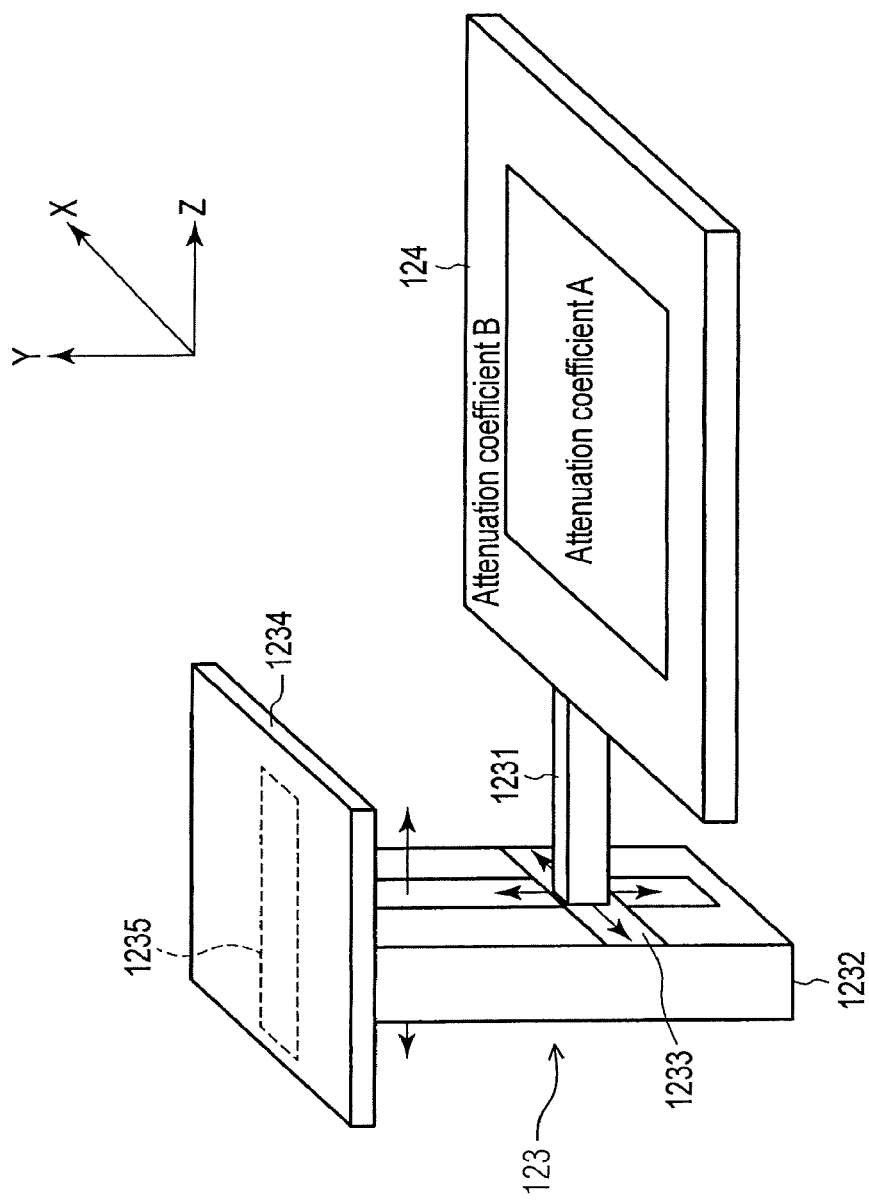
FIG. 7 is a perspective view showing an example of the structure of the X-ray filter support unit of the X-ray diagnostic apparatus according to the first embodiment.

FIG. 7 is a perspective view showing an example of the structure of the X-ray filter support unit 123 of the X-ray diagnostic apparatus according to the first embodiment. As shown in FIG. 7, the X-ray filter support unit 123 includes a first support unit 1231, a second support unit 1232, and a third support unit 1234. The first support unit 1231 supports the X-ray filter 124. The first support unit 1231 has a first slider (not shown) on the coupling surface to the second support unit 1232. As shown in FIG. 7, the second support unit 1232 has a first slide rail 1233 for supporting the first support unit 1231 so as to make it movable in the X and Y directions. The X-ray filter 124 is moved together with the first support unit 1231 in the X and Y directions by moving the first slider along the first slide rail 1233. The second support unit 1232 has a second slider (not shown) on a coupling surface to the third support unit 1234. As shown in FIG. 7, the third support unit 1234 has a second slide rail 1235 for supporting the second support unit 1232 so as to make it movable in the Z direction. The X-ray filter 124 is moved together with the first support unit 1231 and the second support unit 1232 in the Z direction by moving the second support unit 1232 along the second slide rail 1235. The X-ray filter driving unit 122 drives each slider described above. Note that the structure of the X-ray filter support unit 123 shown in FIG. 7 is an example. The structure of the X-ray filter support unit 123 is not limited to that shown in FIG. 7 as long as it can move the X-ray filter 124 in the X, Y, and Z directions (three axis directions) in FIG. 7. The Y-axis direction in FIG. 7 is, for example, parallel to the imaging axis direction. The X-axis direction and the Z-axis direction are perpendicular to each other and are perpendicular to the imaging axis direction.

The dose distribution in the X-ray irradiation range of the X-ray detection unit 14 of the X-ray diagnostic apparatus to which the X-ray filter 124 according to each of the first and second examples is applied will be described with reference to FIGS. 8 and 9.

Figure 8:
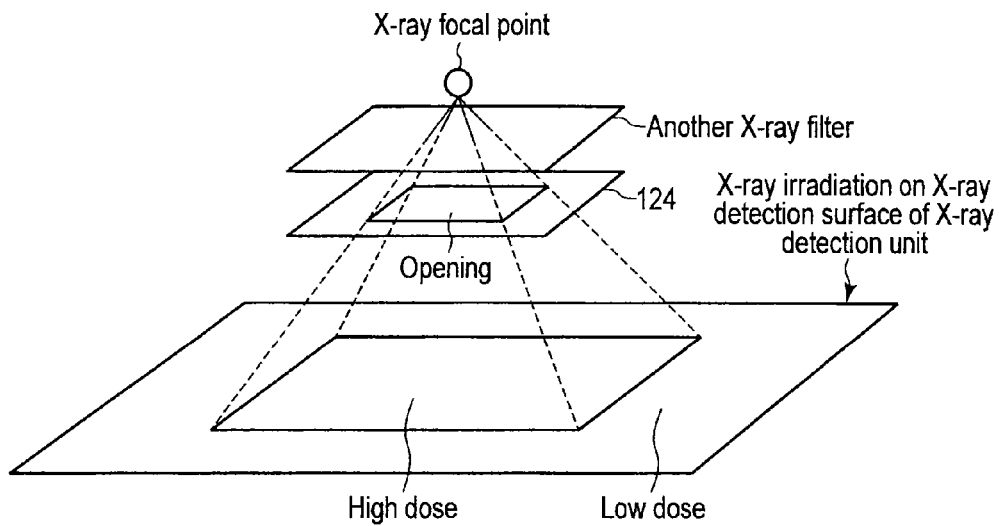
FIG. 8 is a view for explaining a dose distribution in the X-ray irradiation range of the X-ray detection unit of the X-ray diagnostic apparatus to which the X-ray filter according to the first example is applied.

FIG. 8 is a view for explaining the dose distribution in the X-ray irradiation range of the X-ray detection unit 14 of the X-ray diagnostic apparatus to which the X-ray filter 124 according to the first example is applied. As shown in FIG. 8, the X-rays generated from the X-ray focal point and transmitted through the X-ray filter 124 generate, in the X-ray irradiation range on the X-ray detection surface of the X-ray detection unit 14, an irradiation range in which the dose of X-rays is high (to be referred to as a high-dose range hereinafter) and an irradiation range in which the dose of X-rays is low (to be referred to as a low-dose range hereinafter). The size and position of the high-dose range in the X-ray irradiation range respectively correspond to the size and position of the opening of the X-ray filter 124. Note that in the case of the X-ray detection unit 14 having a plurality of portions exhibiting different X-ray reception sensitivities or the X-ray detection unit 14 obtained by combining a plurality of X-ray detection units having different light reception sensitivities, a high-dose range is represented as a range in which the X-ray reception sensitivity of the X-ray detection unit 14 is low, and a low-dose range is represented as a range in which the X-ray reception sensitivity of the X-ray detection unit 14 is high.

Figure 9:
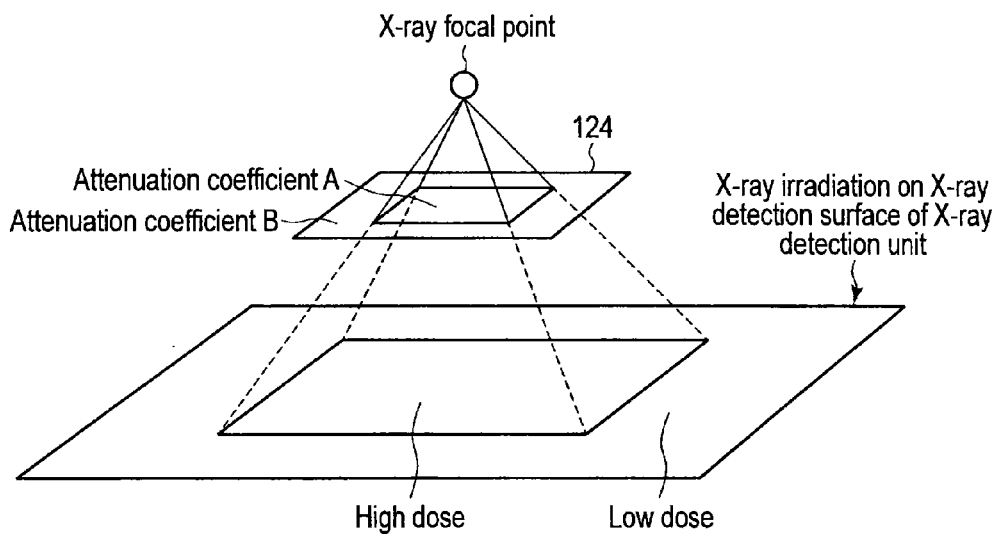
FIG. 9 is a view for explaining a dose distribution in the X-ray irradiation range of the X-ray detection unit of the X-ray diagnostic apparatus to which the X-ray filter according to the second example is applied.

FIG. 9 is a view for explaining the dose distribution in the X-ray irradiation range of the X-ray detection unit 14 of the X-ray diagnostic apparatus to which the X-ray filter 124 according to the second example is applied. As shown in FIG. 9, the X-rays generated from the X-ray focal point and transmitted through the X-ray filter 124 generate a high-dose range and a low-dose range in the X-ray irradiation range on the X-ray detection surface of the X-ray detection unit 14. The size and position of the high-dose range in the X-ray irradiation range respectively correspond to the size and position of the first portion, of the X-ray filter 124, which has the attenuation coefficient A.

A method of controlling the X-ray filter 124 by the X-ray filter control unit 23 of the X-ray diagnostic apparatus according to the first embodiment will be described next. Note that in the following description, the X-ray filter 124 is the one according to the first example.

The X-ray filter control unit 23 controls the X-ray filter driving unit 122 to move the X-ray filter 124 in accordance with a user instruction via the input unit 19. For example, the X-ray filter control unit 23 drives the X-ray filter driving unit 122 so as to make the opening of the X-ray filter 124 correspond to the position and size of the range in which the dose of X-rays is high, which is set in accordance with a user instruction via the input unit 19. The X-ray filter 124 is then moved by the X-ray filter driving unit 122 driven under the control of the X-ray filter control unit 23. In addition, the X-ray filter control unit 23 drives the X-ray filter driving unit 122 to automatically move the X-ray filter 124 in accordance with an output from the X-ray detection unit 14.

Figure 10:
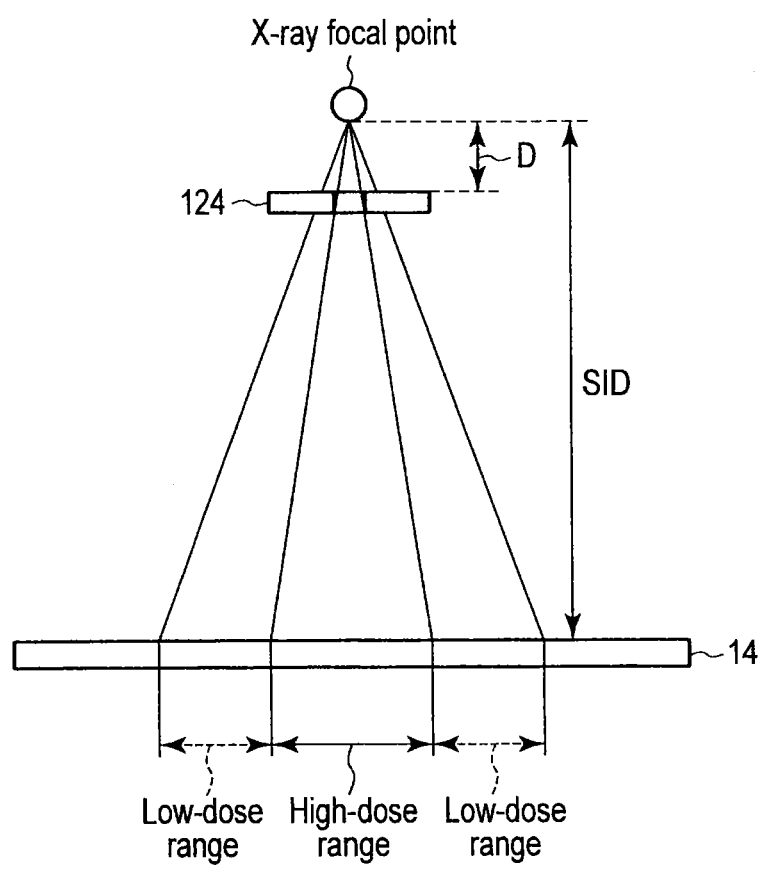
FIG. 10 is a view for explaining automatic control of an X-ray filter driving unit by the X-ray filter control unit of the X-ray diagnostic apparatus according to the first embodiment.

FIG. 10 is a view for explaining automatic control of the X-ray filter driving unit 122 by the X-ray filter control unit 23 of the X-ray diagnostic apparatus according to the first embodiment.

The X-ray filter control unit 23 controls the X-ray filter driving unit 122 to maintain, at a set value, the ratio of a distance SID (Source Image Distance) between the X-ray focal point and the X-ray detection unit 14 to a distance D between the X-ray focal point and the X-ray filter 124. For example, when the X-ray detection unit 14 is moved in the imaging axis direction from the initial position, the SID changes. In accordance with the amount of change in SID, the X-ray filter control unit 23 controls the X-ray filter driving unit 122 to move the X-ray filter 124 so as to maintain the ratio of the SID to the distance D between the X-ray focal point and the X-ray filter 124 at the ratio before the movement of the X-ray detection unit 14. For example, the time when the X-ray detection unit 14 is moved in the imaging axis direction from the initial position is exemplified as the time when the imaging range is widened or narrowed during fluoroscopy using the first X-ray diagnostic apparatus by moving the X-ray detection unit 14.

In addition, the X-ray filter control unit 23 controls the X-ray filter driving unit 122 to maintain the high-dose range at the range set in accordance with a user instruction. More specifically, the X-ray filter control unit 23 specifies the position and size of the high-dose range in the X-ray irradiation range in accordance with the signal output from each of the plurality of X-ray detection elements constituting the X-ray detection unit 14. The X-ray filter control unit 23 then controls the X-ray filter driving unit 122 in accordance with changes in the size and position of the specified high-dose range relative to the size and position of the range set in accordance with a user instruction, and moves the X-ray filter 124. Such control is executed when the imaging range is changed while the range includes a region of interest. Assume that the imaging range is initially set so as to make the central position of a region of interest coincide with the center of the imaging range. When the user changes the imaging range during fluoroscopy, the position of the region of interest in the imaging range is changed. In such a case, the X-ray filter control unit 23 controls the X-ray filter driving unit 122 to make the high-dose range correspond to the initially set region of interest in accordance with a change in imaging range.

The X-ray diagnostic apparatus according to the first embodiment described above can obtain the following effects. The X-ray filter 124 according to the first example in the first embodiment has the opening. In addition, the X-ray filter 124 according to the second example has the plurality of portions with different attenuation coefficients. The X-rays passing through the X-ray filter 124 generate a high-dose range and a low-dose range in the X-ray irradiation range on the X-ray detection surface of the X-ray detection unit 14. Therefore, the X-ray filter 124 of the X-ray diagnostic apparatus according to the first embodiment can partially reduce the dose of X-rays in the dose distribution in the X-ray irradiation range. Therefore, the user can check a partial range corresponding to a high-dose range with a higher image quality than that of a partial range corresponding to a low-dose range. This enables the user to check the region of interest as a high image quality moving image and at the same time check a peripheral portion of the region of interest as a moving image even with an image quality lower than that corresponding to the region of interest.

In addition, the X-ray diagnostic apparatus according to the first embodiment can automatically move the X-ray filter 124 in accordance with a change in region of interest, a change in SID, and a change in imaging range. This enables the X-ray diagnostic apparatus according to the first embodiment to make the high-dose range always correspond to a set region of interest. Therefore, even when a user operation is done to change, for example, the position of the C-arm 11 during X-ray imaging, the region of interest, or the imaging range, the user can check the set region of interest as a moving image with a high image quality during fluoroscopy and at the same time check the remaining range as a moving image with a low image quality.

As described above, the X-ray diagnostic apparatus according to the first embodiment can provide a region of interest as a high-image quality moving image and the remaining region as a low-image quality moving image. This makes it possible to maintain the procedural efficiency of the user while reducing the exposure dose of a patient as compared with the case in which an overall imaging range is obtained as a high-image quality moving image.

Second Embodiment

An X-ray diagnostic apparatus (to be referred to as a second X-ray diagnostic apparatus hereinafter) according to the second embodiment differs from the first X-ray diagnostic apparatus in that it is possible to change the shape and the like of the opening of an X-ray filter 124 of the second X-ray diagnostic apparatus. The second X-ray diagnostic apparatus will be described below. Note that the second X-ray diagnostic apparatus will be described, centering on differences from the first X-ray diagnostic apparatus.

FIG. 11 is a block diagram showing the arrangement of the X-ray diagnostic apparatus according to the second embodiment. As shown in FIG. 11, the second X-ray diagnostic apparatus includes a filter component control unit 24 in addition to the constituent elements of the first X-ray diagnostic apparatus.

The filter component control unit 24 controls a filter component driving unit 128. More specifically, the filter component control unit 24 drives the filter component driving unit 128 to move a plurality of filter components constituting the X-ray filter 124 in accordance with a user instruction via an input unit 19 and an output from an X-ray detection unit 14.

Figure 12:
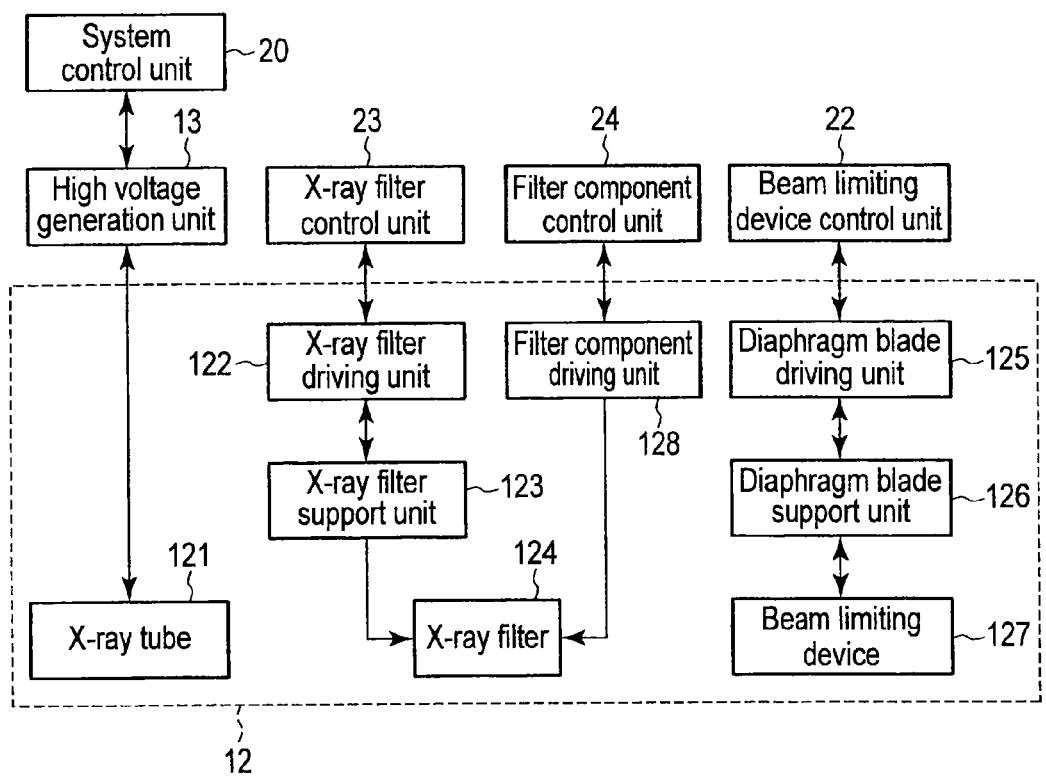
FIG. 12 is a block diagram showing the arrangement of the X-ray irradiation system of the X-ray diagnostic apparatus according to the second embodiment.

FIG. 12 is a block diagram showing the arrangement of an X-ray irradiation system 12 of the X-ray diagnostic apparatus according to the second embodiment. As shown in FIG. 12, the X-ray irradiation system 12 includes an X-ray tube 121, an X-ray filter driving unit 122, an X-ray filter support unit 123, the X-ray filter 124, a diaphragm blade driving unit 125, a diaphragm blade support unit 126, a beam limiting device 127, and the filter component driving unit 128.

The X-ray filter 124 of the second X-ray diagnostic apparatus is constituted by a plurality of filter components. Each of the plurality of filter components has a moving mechanism. The filter component driving unit 128 moves each of the plurality of filter components under the control of the filter component control unit 24. The filter component driving unit 128 is, for example, a driving device such as a motor.

The X-ray filter 124 of the X-ray diagnostic apparatus according to the second embodiment will be described next with reference to FIGS. 13A, 13B, 13C, 14A, 14B, 14C, 15A, 15B, and 15C.

Figure 13A:
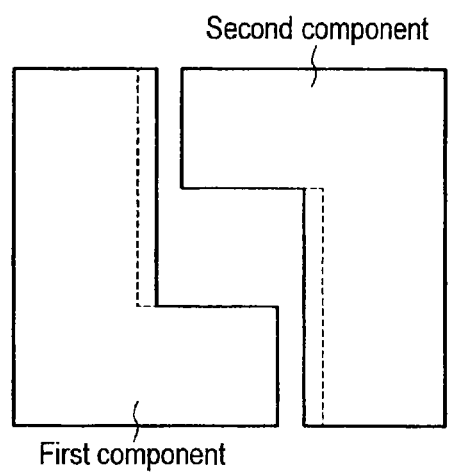
FIG. 13A is an exploded view of the first example of the X-ray filter of the X-ray diagnostic apparatus according to the second embodiment.
Figure 13B:
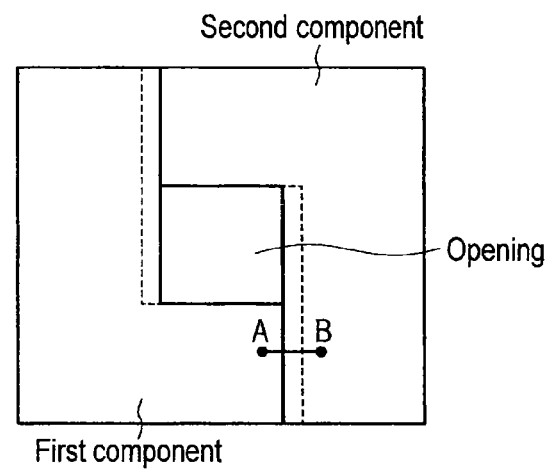
FIG. 13B is a view showing a combined state of the X-ray filter shown in FIG. 13A.
Figure 13C:
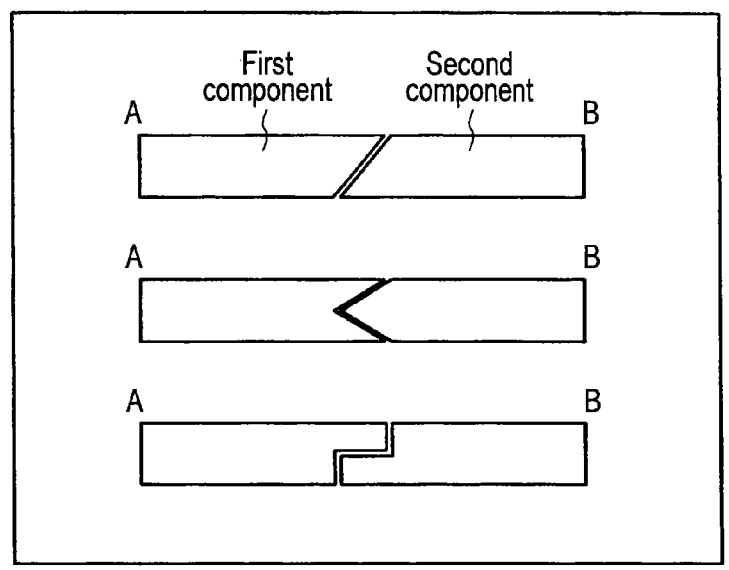
FIG. 13C is a sectional view of the X-ray filter shown in FIG. 13B taken along A-B.

FIGS. 13A, 13B, and 13C are views for explaining an example of the X-ray filter 124 of the X-ray diagnostic apparatus according to the second embodiment.

FIG. 13A is an exploded view of the first example of the X-ray filter 124 of the X-ray diagnostic apparatus according to the second embodiment. As shown in FIG. 13A, the X-ray filter 124 is constituted by first and second components. The first and second components are formed from L-shaped flat metal plates having the same attenuation coefficient.

FIG. 13B is a view showing a combined state of the X-ray filter 124 shown in FIG. 13A. As shown in FIG. 13B, the first and second components are engaged with each other to form the opening of the X-ray filter 124.

FIG. 13C is a sectional view of the X-ray filter 124 shown in FIG. 13B taken along A-B. As shown in FIG. 13C, the first and second components are engaged with each other so as to make the X-ray filter 124 have a uniform thickness. The engagement surfaces have a slidable structure. This slidable structure allows the first and second components to slide relative to each other.

FIGS. 14A, 14B, and 14C are views showing an example of how the opening of the X-ray filter 124 of the X-ray diagnostic apparatus according to the second embodiment is changed.

FIG. 14A is a view showing the X-ray filter 124 according to the first example before a change in the opening. As shown in FIG. 14A, in the initial state in which the first and second components are not moved, for example, the opening of the X-ray filter 124 has a square shape.

FIG. 14B shows the first example in which the opening of the X-ray filter 124 shown in FIG. 14A is changed.

FIG. 14C shows the second example in which the opening of the X-ray filter 124 shown in FIG. 14A is changed. The shape of the opening of the X-ray filter 124 shown in FIG. 14A is changed in the X direction when the first and second components are moved in the X direction and the opposite direction. For example, the size of the opening in the X direction can be decreased by respectively moving the first and second components in the directions indicated by the arrows in FIG. 14B. In contrast, the size of the opening in the X direction can be increased by respectively moving the first and second components in the directions indicated by the arrows in FIG. 14C.

Figure 15A:
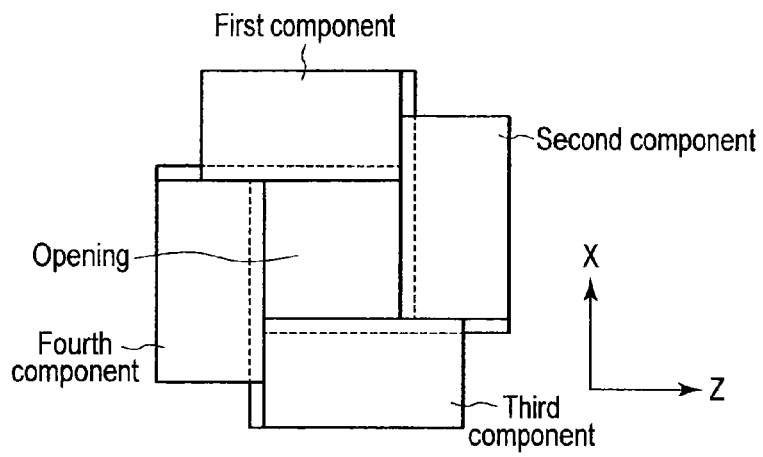
FIG. 15A is a view showing the second example of the X-ray filter before the opening is changed.
Figure 15B:
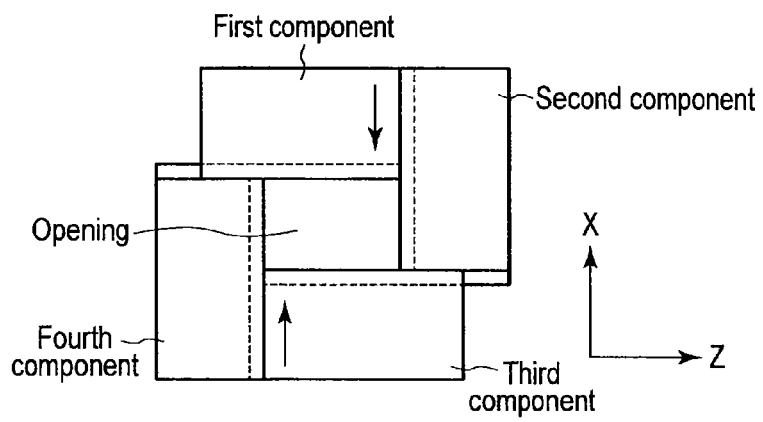
FIG. 15B is a view showing the first example in which the opening of the X-ray filter shown in FIG. 15A is changed.
Figure 15C:
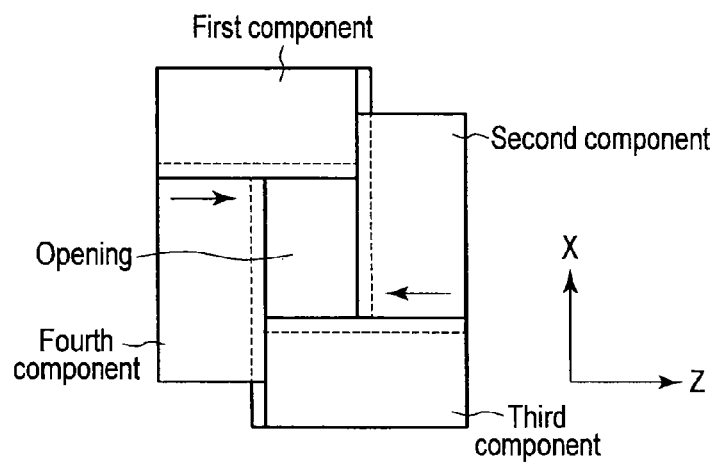
FIG. 15C is a view showing the first example in which the opening of the X-ray filter shown in FIG. 15A is changed.

FIGS. 15A, 15B, and 15C are views for explaining the second example of the X-ray filter 124 of the X-ray diagnostic apparatus according to the second embodiment.

FIG. 15A is a view showing the X-ray filter 124 according to the second example before a change in the opening. As shown in FIG. 15A, the X-ray filter 124 according to the second example is constituted by first, second, third, and fourth components. These four components are, for example, flat metal plates having the same attenuation coefficient. The first component is engaged with the second and fourth components. The third component is engaged with the second and fourth components. The first and third components are not engaged with each other, so are not the second and fourth components. In the state before a change in the opening, i.e., the initial state in which the first to fourth components are not moved, for example, the opening of the X-ray filter 124 has a square shape. Note that the filter component driving unit 128 can independently control each of the four components.

FIG. 15B shows the first example in which the opening of the X-ray filter 124 shown in FIG. 15A is changed.

FIG. 15C shows the second example in which the opening of the X-ray filter 124 shown in FIG. 15A is changed. The shape of the opening in the X direction can be changed by respectively moving the first and third components in the directions indicated by the arrows in FIG. 15B. On the other hand, the shape of the opening in the Z direction can be changed by respectively moving the second and fourth components in the directions indicated by the arrows in FIG. 15C.

In summary, the X-ray filter 124 of the first example of the X-ray diagnostic apparatus according to the second embodiment shown in FIG. 14A and the X-ray filter 124 of the second example of the X-ray diagnostic apparatus according to the second embodiment shown in FIG. 15A each can change the shape and size of the opening. This makes it possible to increase the degree of freedom in changing the X-ray irradiation range corresponding to the opening.

The X-ray diagnostic apparatus according to the second embodiment described above can obtain the following effects in addition to the effects obtained by the X-ray diagnostic apparatus according to the first embodiment. The X-ray filter 124 according to the second embodiment has a mechanism for changing the shape, size, and the like of the opening. For this reason, the X-ray filter 124 according to the second embodiment can decide a high-dose range more precisely than the X-ray filter 124 of the first example according to the first embodiment. Therefore, the X-ray filter 124 according to the second embodiment has the effect of reducing exposure of an object in addition to the effects of the X-ray filter 124 of the first example according to the first embodiment.

Third Embodiment

An X-ray diagnostic apparatus according to the third embodiment differs from the first X-ray diagnostic apparatus and the X-ray diagnostic apparatus according to the second embodiment in that it can select an X-ray filter 124 with which the dose of X-rays in a high-dose range becomes a predetermined amount from a plurality of X-ray filters 124 in accordance with a user instruction, examination information of an object, patient information of the object, and the like. The third X-ray diagnostic apparatus will be described below. Note that the third X-ray diagnostic apparatus will be described, centering on differences from the first and second X-ray diagnostic apparatuses.

Figure 16:
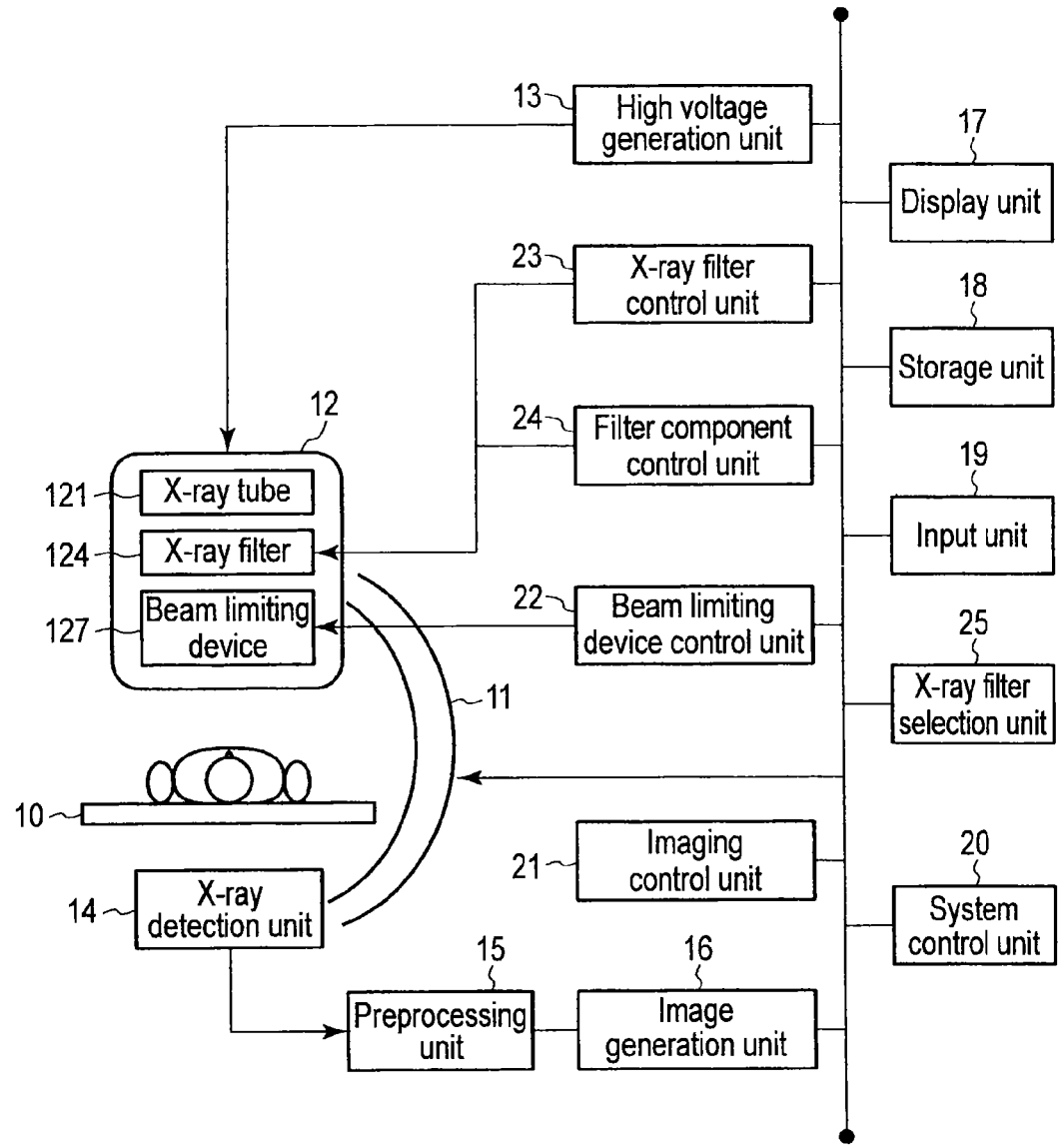
FIG. 16 is a block diagram showing the arrangement of an X-ray diagnostic apparatus according to the third embodiment.

FIG. 16 is a block diagram showing the arrangement of the X-ray diagnostic apparatus according to the third embodiment. As shown in FIG. 16, the third X-ray diagnostic apparatus includes an X-ray filter selection unit 25 in addition to the constituent elements of the first X-ray diagnostic apparatus.

The X-ray filter selection unit 25 selects the X-ray filter 124 with which the dose of X-rays in a low-dose range becomes a predetermined dose from the plurality of X-ray filters 124 with different attenuation coefficients in accordance with examination information of an object, patient information, and the like. Examination information is information concerning, for example, an examination region of an object, an examination direction, and the concentration of a contrast medium. Patient information includes, for example, the age, sex, height, weight, exposure information, and exposure history information of a patient.

The X-ray filter selection unit 25 also selects the X-ray filter 124 from the plurality of X-ray filters 124 with different opening shapes in accordance with the shape of the range set in accordance with a user instruction.

In addition, the X-ray filter selection unit 25 selects the X-ray filter 124 from the plurality of X-ray filters 124 with different opening sizes in accordance with the size of the range set in accordance with a user instruction.

An X-ray filter support unit 123 includes a filter installation unit 1236 for setting the plurality of X-ray filters 124, in addition to a structure which movably supports the X-ray filters 124 described above.

FIG. 17 is a view showing an example of the structure of the X-ray filter support unit 123 of the X-ray diagnostic apparatus according to the third embodiment. Assume that in the description made with reference to FIG. 17, the X-ray filter 124 is identical to the X-ray filter 124 according to the second example described above. As shown in FIG. 17, the X-ray filter support unit 123 includes the filter installation unit 1236, a first support unit 1231, a second support unit 1232, and a third support unit 1234. As shown in, for example, FIG. 17, the filter installation unit 1236 is formed from a metal disk or the like, with its side surface being provided with a rotatable structure, e.g., a rail. The filter installation unit 1236 has, on the metal disk, a plurality of installation positions for the installation of the plurality of X-ray filters 124 with different attenuation coefficients. A plurality of X-ray filters 124 are installed at a plurality of installation positions. Note that the plurality of X-ray filters 124 correspond to the first example and may include a plurality of X-ray filters 124 with different attenuation coefficients, a plurality of X-ray filters 124 with different opening shapes, and a plurality of X-ray filters 124 with different opening sizes. The first support unit 1231 rotatably supports the filter installation unit 1236. The first support unit 1231 includes a rotating slider (not shown) for rotating the filter installation unit 1236 along the rail provided on the filter installation unit 1236 at the coupling surface to the filter installation unit 1236. An X-ray filter control unit 23 controls an X-ray filter driving unit 122 to move the X-ray filter 124 selected by the X-ray filter selection unit 25 to the operating filter installation position in FIG. 17. Note that the structure for the installation of the plurality of X-ray filters 124 shown in FIG. 17 is an example. For example, each of the plurality of X-ray filters 124 may be supported so as to be independently movable instead of being installed on the disk, as shown in FIG. 17. In this case, the X-ray filter control unit 23 controls the X-ray filter driving unit 122 corresponding to the X-ray filter 124 selected by the X-ray filter selection unit 25 to move the selected X-ray filter 124 to the operating filter installation position in FIG. 17. Alternatively, the X-ray filter selection unit 25 may select the X-ray filter 124 to be used from the plurality of X-ray filters 124 upon combining the X-ray filter 124 described above.

Figure 18:
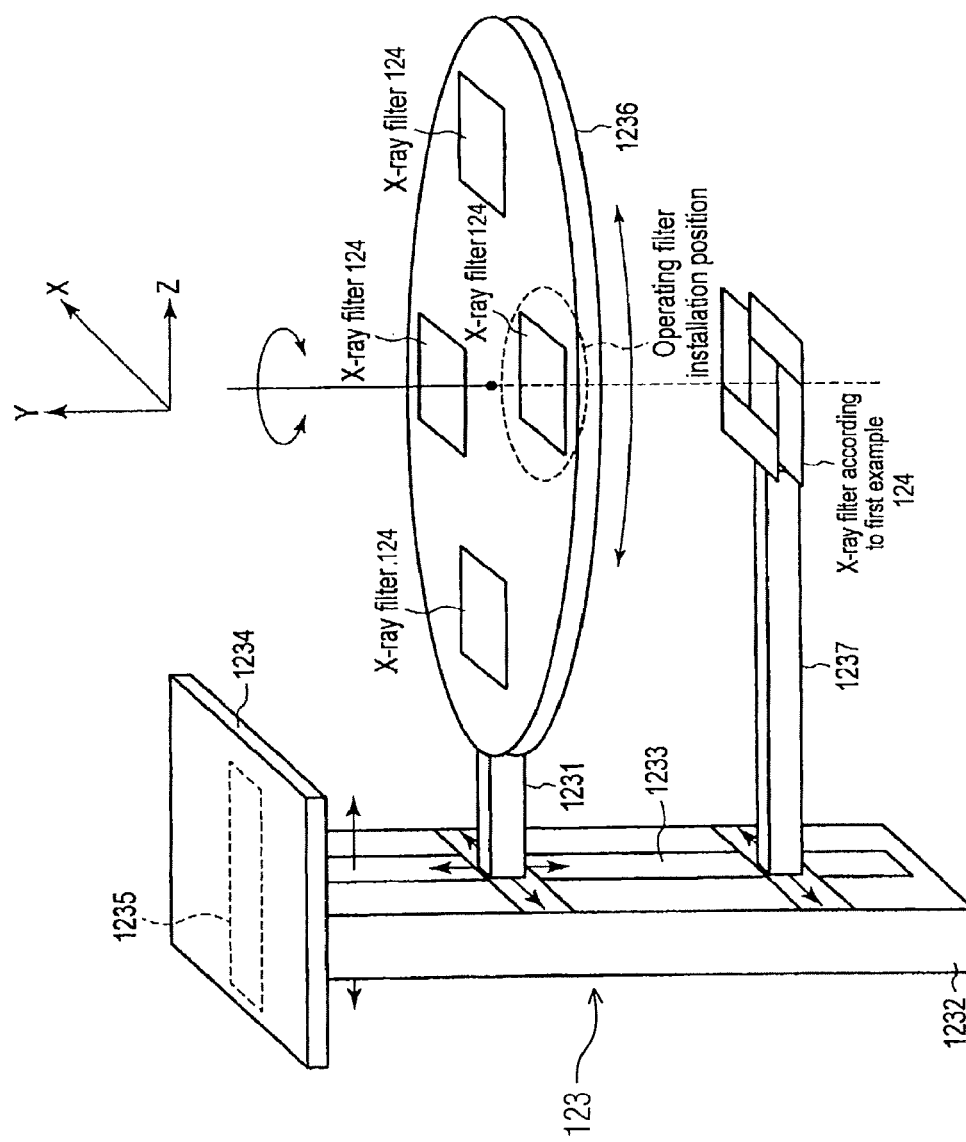
FIG. 18 is a perspective view showing another example of the structure of the X-ray filter support unit of the X-ray diagnostic apparatus according to the third embodiment.

FIG. 18 is a view showing another example of the structure of the X-ray filter support unit 123 of the X-ray diagnostic apparatus according to the third embodiment. The structure shown in FIG. 18 shows an example of installing the plurality of X-ray filters 124 in the imaging axis direction. The X-ray filter support unit 123 includes a fourth support unit 1237 for supporting another X-ray filter in addition to the structure of the X-ray filter support unit 123 shown in FIG. 17. Referring to FIG. 18, another X-ray filter is the X-ray filter 124 shown in FIG. 15A. When combining the X-ray filter 124, it is possible to combine the X-ray filter 124 described above in any form as long as it can generate a high-dose range and a low-dose range in the X-ray imaging range.

The X-ray diagnostic apparatus according to the third embodiment described above can obtain the following effects in addition to the effects of the X-ray diagnostic apparatuses according to the first and second embodiments. The X-ray diagnostic apparatuses according to the first and second embodiments use the X-ray filter 124 installed in advance. That is, the difference in dose between the high-dose range and the low-dose range is almost fixed unless the X-ray filter 124 is manually changed or a plurality of X-ray filters 124 are used. In contrast to this, the X-ray diagnostic apparatus according to the third embodiment can select the X-ray filter 124 for making the dose in a low-dose range become a predetermined amount from the plurality of X-ray filters 124 with different attenuation coefficients in accordance with the patient information, examination information, and the like of an object. This enables the X-ray diagnostic apparatus according to the third embodiment to decide a high-dose range and a low-dose range in accordance with an object as compared with the X-ray diagnostic apparatuses according to the first and second embodiments. That is, the X-ray diagnostic apparatus according to the third embodiment can reduce the exposure dose of an object as compared with the X-ray diagnostic apparatuses according to the first and second embodiments.

Fourth Embodiment

An X-ray diagnostic apparatus (to be referred to as a fourth X-ray diagnostic apparatus hereinafter) according to the fourth embodiment differs from the X-ray diagnostic apparatuses according to the first, second, and third embodiments in that an X-ray filter control unit 23 drives an X-ray filter driving unit 122 to move an X-ray filter 124 in accordance with a change in the position of a feature point on the image displayed on a display unit 17. The fourth X-ray diagnostic apparatus obtained by adding the above function to the first X-ray diagnostic apparatus will be described below. Note that the above function may be added to the second X-ray diagnostic apparatus and the third X-ray diagnostic apparatus. The fourth X-ray diagnostic apparatus will be described, centering on differences from the first, second, and third X-ray diagnostic apparatuses.

Figure 19:
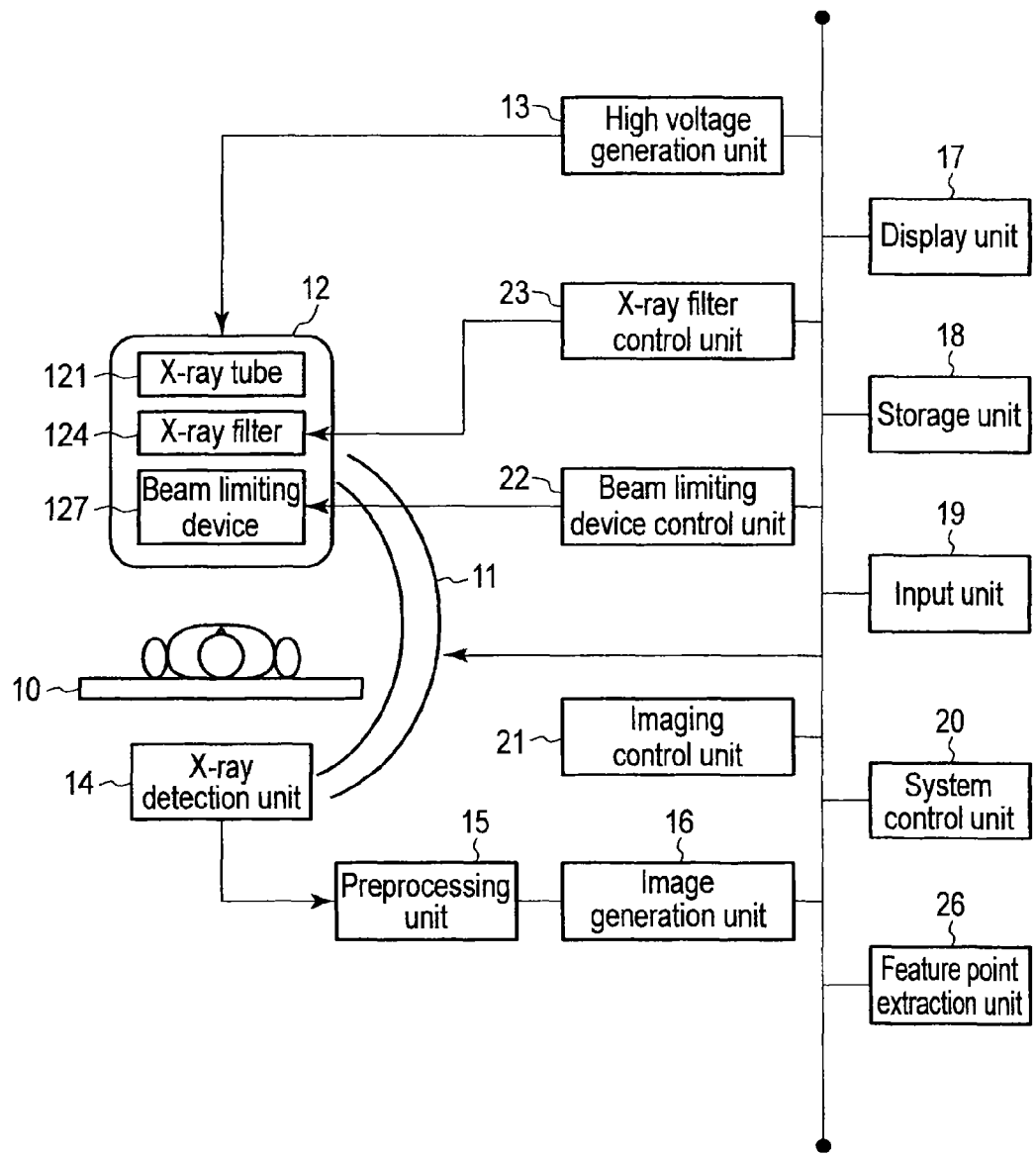
FIG. 19 is a block diagram showing the arrangement of an X-ray diagnostic apparatus according to the fourth embodiment.

FIG. 19 is a block diagram showing the arrangement the X-ray diagnostic apparatus according to the fourth embodiment. As shown in FIG. 19, the fourth X-ray diagnostic apparatus includes a feature point extraction unit 26 in addition to the constituent elements of the first X-ray diagnostic apparatus.

The feature point extraction unit 26 extracts the feature point set by the user in advance from an X-ray image concerning an object, which is displayed on the display unit 17, by threshold processing or the like. A feature point indicates a characteristic portion which the user wants to see with a high image quality during surgery or the like. A feature point is, for example, the distal end of a catheter.

The X-ray filter control unit 23 controls the X-ray filter driving unit 122 to move the X-ray filter 124 based on an output from the feature point extraction unit 26. More specifically, the X-ray filter control unit 23 specifies an automatically set range centered on the position of the feature point on the image which is extracted by the feature point extraction unit 26. The X-ray filter control unit 23 then drives the X-ray filter driving unit 122 to move the X-ray filter 124 so as to make a high-dose range correspond to the automatically set range.

FIG. 20 is a view for explaining the automatically set range set by the X-ray filter control unit 23 of the X-ray diagnostic apparatus according to the fourth embodiment. FIG. 20 shows the fluoroscopic image displayed on the display unit 17. Assume that the user is manipulating a catheter while visually recognizing the fluoroscopic image displayed on the display unit 17. Assume that in the description made with reference to FIG. 20, the user has already set a feature point at the distal end of the catheter. First of all, the feature point extraction unit 26 specifies the position of the distal end of the catheter on the image. As shown in FIG. 20, the X-ray filter control unit 23 sets an automatically set range having a rectangular shape, with set margins being added from the position of the feature point in four directions (the X and Y directions in FIG. 20). The X-ray filter control unit 23 drives the X-ray filter driving unit 122 to move the X-ray filter 124 in accordance with the amount of change in the position of the automatically set range.

The X-ray diagnostic apparatus according to the fourth embodiment described above can obtain the following effects in addition to the effects of the X-ray diagnostic apparatuses according to the first, second, and third embodiments.

When the X-ray diagnostic apparatus according to another embodiment is used, the user designates a region of interest, and movement control of the X-ray filter 124 is performed to make a high-dose range correspond to the region of interest. On the other hand, the X-ray diagnostic apparatus according to the fourth embodiment can set an automatically set range in accordance with the position of the feature point displayed on the display unit 17. In order to make the set automatically set range correspond to the high-dose range, it is possible to move the X-ray filter 124 by driving the X-ray filter driving unit 122. This makes it possible to suppress a high-dose range to a minimum range when a region of interest momentarily changes. Assume that a region near the distal end of the catheter is set as a region of interest, and the catheter is moved during the manipulation of the catheter. Even in this case, a region of interest is set in a range including a region near the distal end of the catheter, and a high-dose range can be made to correspond to the set region of interest. Using the X-ray diagnostic apparatus according to the fourth embodiment makes it unnecessary for the user to manually set a region of interest again every time he/she moves the catheter. In addition, since a region of interest is automatically set, a high-dose range is suppressed to a minimum range, and the exposure dose of the patient can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising:
   an X-ray tube configured to generate X-rays;
   an X-ray detector configured to detect X-rays generated from the X-ray tube and transmitted through an object;
   an X-ray filter configured to be arranged between the X-ray tube and the object and having an opening; and
   an X-ray filter support unit configured to support the X-ray filter so as to make the X-ray filter movable along an imaging axis direction of the X-rays.

2. The X-ray diagnostic apparatus of claim 1, further comprising another X-ray filter configured to be arranged at a position located between the X-ray tube and the object and shifted along the imaging axis with respect to the X-ray filter.

3. The X-ray diagnostic apparatus of claim 1, wherein the X-ray filter support unit supports the X-ray filter so as to make the X-ray filter movable along two axes perpendicular to the imaging axis.

4. The X-ray diagnostic apparatus of claim 1, further comprising an X-ray filter driving unit configured to rotate and move the X-ray filter about an axis parallel to the imaging axis.

5. The X-ray diagnostic apparatus of claim 1, further comprising:
   an X-ray filter driving unit configured to move the X-ray filter; and
   an X-ray filter control unit configured to control the X-ray filter driving unit in accordance with a first range on a detection surface of the X-ray detector in which X-ray reception sensitivity is lower than X-ray reception sensitivity of a second range on the detection surface of the X-ray detector.

6. The X-ray diagnostic apparatus of claim 5, wherein the X-ray filter control unit controls the X-ray filter driving unit in accordance with a change in dose distribution in the X-ray irradiation range to maintain an irradiation range corresponding to the opening in a range set in accordance with an instruction from a user.

7. The X-ray diagnostic apparatus of claim 5, further comprising:
   an image generation unit configured to generate data of an X-ray image concerning the object based on an output from the X-ray detector; and
   a feature point extraction unit configured to extract a feature point from the X-ray image by threshold processing,
   wherein the X-ray filter control unit controls the X-ray filter driving unit to include the extracted feature point in the irradiation range corresponding to the opening.

8. The X-ray diagnostic apparatus of claim 1, wherein the X-ray filter includes a plurality of filter components.

9. The X-ray diagnostic apparatus of claim 8, further comprising:
   a filter component driving unit configured to move the plurality of filter components to change at least one of a position of the opening of the X-ray filter and a size of the opening; and
   a filter component control unit configured to control the filter component driving unit.

10. The X-ray diagnostic apparatus of claim 9, wherein the filter component control unit controls the filter component driving unit in accordance with a range of the X-ray detector in which X-ray reception sensitivity is low.

11. The X-ray diagnostic apparatus of claim 9, wherein the filter component control unit controls the filter component driving unit in accordance with a change in dose distribution in the X-ray irradiation range to maintain an irradiation range corresponding to the opening in a range set in accordance with an instruction from a user.

12. The X-ray diagnostic apparatus of claim 1, wherein the X-ray filter support unit moves according to change of an SID so as to maintain a ratio of the SID to a distance between an X-ray focal point and the X-ray filter.

13. An X-ray diagnostic apparatus comprising:
   an X-ray tube configured to generate X-rays;
   an X-ray detector configured to detect X-rays generated from the X-ray tube and transmitted through an object;
   a plurality of types of X-ray filters configured to be arranged between the X-ray tube and the object; and
   an X-ray filter support unit configured to support the plurality of types of X-ray filters so as to make the plurality of types of X-ray filters movable along an imaging axis direction of the X-rays, wherein the plurality of types of X-ray filters include respective attenuation coefficients different from each other.

14. The X-ray diagnostic apparatus of claim 13, further comprising a filter selection unit configured to select, from the plurality of types of X-ray filters with different attenuation coefficients, one of the plurality of types of X-ray filters which reduces a dose of X-rays reaching a range of the X-ray detector in which X-ray reception sensitivity is high to a dose lower than a predetermined dose, in accordance with examination information of the object.

15. A diagnostic method comprising the steps of:
arranging an X-ray filter between an X-ray tube and an object;
irradiating the object with X-rays using the X-ray tube;
detecting X-rays generated from the X-ray tube and transmitted through the object; and
moving the X-ray filter along an imaging axis direction of the X-rays.

16. The diagnostic method of claim 15, wherein the moving step includes moving, according to change of an SID, the X-ray filter along the imaging axis direction of the X-rays so as to maintain a ratio of the SID to a distance between an X-ray focal point and the X-ray filter.

17. The diagnostic method of claim 15, wherein the moving step includes moving the X-ray filter along the imaging axis direction of the X-rays so as to maintain a high-dose range of the X-rays in a first range on a detection surface of an X-ray detector, X-ray reception sensitivity of the first range being lower than X-ray reception sensitivity of a second range on the detection surface of the X-ray detector.

* * * * *